United States Patent
Lurie et al.

(10) Patent No.: US 10,406,069 B2
(45) Date of Patent: *Sep. 10, 2019

(54) DEVICE FOR ELEVATING THE HEAD AND CHEST FOR TREATING LOW BLOOD FLOW STATES

(71) Applicant: Keith G. Lurie, Minneapolis, MN (US)

(72) Inventors: Keith G. Lurie, Minneapolis, MN (US); Bayert Salverda, Inver Grove Heights, MN (US)

(73) Assignee: Keith G. Lurie, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,466

(22) Filed: May 22, 2018

(65) Prior Publication Data

US 2018/0333328 A1    Nov. 22, 2018

Related U.S. Application Data

(63) Continuation-in-part of application No. 15/850,827, filed on Dec. 21, 2017, which is a
(Continued)

(51) Int. Cl.
*A61H 31/00* (2006.01)
*A61G 7/07* (2006.01)
(Continued)

(52) U.S. Cl.
CPC .............. *A61H 31/008* (2013.01); *A61G 7/07* (2013.01); *A61G 13/009* (2013.01);
(Continued)

(58) Field of Classification Search
CPC ..... A61H 31/00; A61H 31/008; A61H 1/0229; A61G 7/005
See application file for complete search history.

(56) References Cited

U.S. PATENT DOCUMENTS

| | | |
|---|---|---|
| 1,995,583 A | 3/1935 | Sanderson |
| 3,461,858 A | 8/1969 | Irving |

(Continued)

FOREIGN PATENT DOCUMENTS

| | | |
|---|---|---|
| EP | 2289477 A1 | 9/2014 |
| WO | 2015/127102 A2 | 8/2015 |
| WO | 2017/066770 A1 | 4/2017 |

OTHER PUBLICATIONS

Voelckel et al "The effects of positive end-expiratory pressure during active compression decompression cardiopulmonary resuscitation with the inspiratory threshold valve." Anesthesia and Analgesia. Apr. 2001: 92(4): 967-74.

(Continued)

*Primary Examiner* — Justine R Yu
*Assistant Examiner* — Christopher E Miller
(74) *Attorney, Agent, or Firm* — Kilpatrick Townsend & Stockton LLP

(57) ABSTRACT

A method of increasing blood flow to the head includes causing an individual's blood to circulate while the individual's heart and head are at a first elevation position, elevating the individual's heart and head to a second elevation position that is above the first elevation position, and causing the individual's blood to circulate while the individual's heart and head are at the second elevation position.

26 Claims, 27 Drawing Sheets

Related U.S. Application Data continuation-in-part of application No. 15/601,494, filed on May 22, 2017, which is a continuation-in-part of application No. 15/285,063, filed on Oct. 4, 2016, which is a continuation-in-part of application No. 15/160,492, filed on May 20, 2016, which is a continuation-in-part of application No. 15/133,967, filed on Apr. 20, 2016, now Pat. No. 9,801,782, which is a continuation-in-part of application No. 14/996,147, filed on Jan. 14, 2016, now Pat. No. 9,750,661, which is a continuation-in-part of application No. 14/935,262, filed on Nov. 6, 2015, now Pat. No. 9,707,152, said application No. 14/935,262 is a continuation-in-part of application No. 14/677,562, filed on Apr. 2, 2015, now Pat. No. 10,092,481, which is a continuation of application No. 14/626,770, filed on Feb. 19, 2015, now Pat. No. 10,245,209.

(60) Provisional application No. 62/509,469, filed on May 22, 2017, provisional application No. 62/242,655, filed on Oct. 16, 2015, provisional application No. 62/087,717, filed on Dec. 4, 2014, provisional application No. 62/000,836, filed on May 20, 2014, provisional application No. 61/941,670, filed on Feb. 19, 2014.

(51) Int. Cl.
*A61G 13/00* (2006.01)
*A61M 16/00* (2006.01)
*A61G 13/12* (2006.01)

(52) U.S. Cl.
CPC .......... *A61H 31/006* (2013.01); *A61H 31/007* (2013.01); *A61M 16/0057* (2013.01); *A61G 13/121* (2013.01); *A61G 13/122* (2013.01); *A61G 2200/327* (2013.01); *A61G 2203/10* (2013.01); *A61H 2201/018* (2013.01); *A61H 2201/10* (2013.01); *A61H 2201/123* (2013.01); *A61H 2201/1607* (2013.01); *A61H 2201/1626* (2013.01); *A61H 2203/0456* (2013.01); *A61H 2205/084* (2013.01); *A61H 2230/045* (2013.01); *A61H 2230/206* (2013.01); *A61H 2230/208* (2013.01); *A61H 2230/255* (2013.01); *A61H 2230/305* (2013.01); *A61H 2230/405* (2013.01)

(56) References Cited

U.S. PATENT DOCUMENTS

| | | | |
|---|---|---|---|
| 3,509,899 A | 5/1970 | Hewson | |
| 3,804,082 A | 4/1974 | Tarjan et al. | |
| 3,866,604 A * | 2/1975 | Curless | A61H 9/0078 601/152 |
| 3,870,038 A | 3/1975 | Arblaster | |
| 3,985,126 A | 10/1976 | Baralow | |
| 4,060,079 A | 11/1977 | Reinhold, Jr. | |
| 4,095,590 A | 6/1978 | Harrigan | |
| 4,168,554 A * | 9/1979 | Hindes | A61H 31/008 5/625 |
| 4,194,732 A | 3/1980 | Liebman | |
| 4,362,336 A | 12/1982 | Zapf et al. | |
| 4,534,075 A | 8/1985 | Schnitzler | |
| 4,915,095 A | 4/1990 | Chun | |
| 5,048,136 A | 9/1991 | Popitz | |
| 5,316,907 A | 5/1994 | Lurie | |
| 5,399,148 A | 3/1995 | Waide et al. | |
| 5,400,448 A | 3/1995 | Zwickey | |
| 5,423,772 A | 6/1995 | Lurie | |
| 5,454,779 A | 10/1995 | Lurie et al. | |
| 5,487,722 A | 1/1996 | Sherman et al. | |
| 5,490,820 A | 2/1996 | Schock et al. | |
| 5,538,002 A | 7/1996 | Boussignac et al. | |
| 5,549,581 A | 8/1996 | Lurie | |
| 5,551,420 A | 9/1996 | Lurie et al. | |
| 5,588,422 A | 12/1996 | Lurie | |
| 5,618,665 A | 4/1997 | Lurie | |
| 5,634,222 A | 6/1997 | Zwickey | |
| 5,643,231 A | 7/1997 | Lurie | |
| 5,645,522 A | 7/1997 | Lurie et al. | |
| 5,692,498 A | 12/1997 | Lurie et al. | |
| 5,722,963 A | 3/1998 | Lurie | |
| 5,730,122 A | 3/1998 | Lurie | |
| 5,730,136 A * | 3/1998 | Laufer | A61B 5/02007 600/454 |
| 5,827,893 A | 10/1998 | Lurie | |
| 5,919,210 A | 7/1999 | Lurie | |
| 5,984,909 A | 11/1999 | Lurie | |
| 6,001,085 A | 12/1999 | Lurie | |
| 6,029,667 A | 2/2000 | Lurie | |
| 6,062,219 A | 5/2000 | Lurie et al. | |
| 6,078,834 A | 6/2000 | Lurie | |
| 6,142,962 A | 11/2000 | Mollenauer | |
| 6,155,257 A | 12/2000 | Lurie et al. | |
| 6,224,562 B1 | 5/2001 | Lurie et al. | |
| 6,234,916 B1 | 5/2001 | Carusillo et al. | |
| 6,234,985 B1 | 5/2001 | Lurie et al. | |
| 6,277,107 B1 | 8/2001 | Lurie | |
| 6,312,399 B1 | 11/2001 | Lurie et al. | |
| 6,357,065 B1 | 3/2002 | Adams | |
| 6,371,119 B1 | 4/2002 | Zadini et al. | |
| 6,425,393 B1 | 7/2002 | Lurie et al. | |
| 6,446,288 B1 | 9/2002 | Pi | |
| 6,446,962 B1 | 9/2002 | Pi | |
| 6,459,933 B1 | 10/2002 | Lurie et al. | |
| 6,463,327 B1 | 10/2002 | Lurie et al. | |
| 6,486,206 B1 | 11/2002 | Lurie | |
| 6,526,973 B1 | 3/2003 | Lurie et al. | |
| 6,587,726 B2 | 7/2003 | Lurie et al. | |
| 6,604,523 B2 | 8/2003 | Lurie et al. | |
| 6,656,166 B2 | 12/2003 | Lurie | |
| 6,751,818 B2 | 6/2004 | Troop | |
| 6,776,156 B2 | 8/2004 | Lurie et al. | |
| 6,863,656 B2 | 3/2005 | Lurie | |
| 6,935,336 B2 | 8/2005 | Lurie et al. | |
| 6,938,618 B2 | 9/2005 | Lurie et al. | |
| 6,986,349 B2 | 1/2006 | Lurie | |
| 7,044,128 B2 | 5/2006 | Lurie | |
| 7,056,296 B2 | 6/2006 | Sherman et al. | |
| 7,060,041 B1 | 6/2006 | Weil et al. | |
| 7,082,945 B2 | 8/2006 | Lurie | |
| 7,174,891 B2 | 2/2007 | Lurie et al. | |
| 7,185,649 B2 | 3/2007 | Lurie | |
| 7,195,012 B2 | 3/2007 | Lurie | |
| 7,195,013 B2 | 3/2007 | Lurie | |
| 7,204,251 B2 | 4/2007 | Lurie | |
| 7,210,480 B2 | 5/2007 | Lurie et al. | |
| 7,275,542 B2 | 10/2007 | Lurie et al. | |
| 7,296,312 B2 | 11/2007 | Menkedick | |
| 7,311,668 B2 | 12/2007 | Lurie et al. | |
| 7,569,021 B2 | 8/2009 | Sebelius et al. | |
| 7,682,312 B2 | 3/2010 | Lurie | |
| 7,766,011 B2 | 8/2010 | Lurie | |
| 7,836,881 B2 | 11/2010 | Lurie et al. | |
| 7,899,526 B2 | 3/2011 | Benditt et al. | |
| 8,011,367 B2 | 9/2011 | Lurie et al. | |
| 8,151,790 B2 | 4/2012 | Lurie et al. | |
| 8,210,176 B2 | 7/2012 | Metzger et al. | |
| 8,291,534 B2 | 10/2012 | Karlson | |
| 8,408,204 B2 | 4/2013 | Lurie | |
| 8,690,807 B2 * | 4/2014 | Hiebert | A61F 5/05833 602/13 |
| 8,702,633 B2 | 4/2014 | Voss et al. | |
| 8,752,220 B2 | 6/2014 | Soderberg et al. | |
| 8,755,902 B2 | 6/2014 | Lurie et al. | |
| 9,707,152 B2 | 7/2017 | Lurie | |
| 9,750,661 B2 * | 9/2017 | Lurie | A61G 13/1215 |
| 9,801,782 B2 * | 10/2017 | Lurie | A61H 31/005 |
| 2002/0002347 A1 | 1/2002 | Kelly et al. | |

(56) References Cited

U.S. PATENT DOCUMENTS

| | | |
|---|---|---|
| 2002/0069878 A1 | 6/2002 | Lurie et al. |
| 2002/0170562 A1 | 11/2002 | Lurie et al. |
| 2003/0062040 A1 | 4/2003 | Lurie et al. |
| 2004/0016428 A9 | 1/2004 | Lurie |
| 2004/0058305 A1 | 3/2004 | Lurie et al. |
| 2004/0116840 A1 | 6/2004 | Cantrell et al. |
| 2004/0200474 A1 | 10/2004 | Lurie |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0162077 A1 | 7/2006 | McDaniel et al. |
| 2006/0258964 A1* | 11/2006 | Biondo ............ A61H 9/0078 601/152 |
| 2006/0277683 A1 | 12/2006 | Lamire et al. |
| 2007/0021683 A1 | 1/2007 | Benditt et al. |
| 2007/0157385 A1* | 7/2007 | Lemire ............ A61G 7/005 5/600 |
| 2007/0277826 A1 | 12/2007 | Lurie |
| 2008/0045867 A1 | 2/2008 | Jensen et al. |
| 2008/0047555 A1 | 2/2008 | Lurie et al. |
| 2008/0255482 A1 | 10/2008 | Lurie |
| 2009/0062701 A1 | 3/2009 | Yannopoulos et al. |
| 2009/0277447 A1 | 11/2009 | Voss et al. |
| 2009/0308400 A1 | 12/2009 | Wilson et al. |
| 2010/0031961 A1 | 2/2010 | Schmidt |
| 2010/0179442 A1 | 7/2010 | Lurie |
| 2010/0319691 A1 | 12/2010 | Lurie et al. |
| 2011/0030141 A1* | 2/2011 | Soderberg ............ A61G 7/015 5/600 |
| 2011/0047709 A1 | 3/2011 | Tarsaud et al. |
| 2011/0083271 A1* | 4/2011 | Bhai ............ A61G 7/015 5/610 |
| 2011/0098612 A1 | 4/2011 | Lurie |
| 2011/0132377 A1* | 6/2011 | Phillips ............ A61H 9/0078 128/845 |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016179 A1* | 1/2012 | Paradis ............ A61H 9/0078 600/17 |
| 2012/0042881 A1 | 2/2012 | Paulussen et al. |
| 2012/0109027 A1* | 5/2012 | Gozelski, Jr. ......... A61G 7/005 601/26 |
| 2012/0203147 A1 | 8/2012 | Lurie et al. |
| 2012/0260428 A1 | 10/2012 | Franklin |
| 2012/0266383 A1 | 10/2012 | Pi |
| 2012/0330199 A1 | 12/2012 | Lurie et al. |
| 2012/0330200 A1 | 12/2012 | Voss et al. |
| 2013/0231593 A1 | 9/2013 | Yannopoulos et al. |
| 2014/0005566 A1 | 1/2014 | Homuth et al. |
| 2014/0048061 A1 | 2/2014 | Yannopoulos et al. |
| 2014/0082842 A1 | 3/2014 | Jackson |
| 2014/0171839 A1 | 6/2014 | Fleming |
| 2014/0276269 A1 | 9/2014 | Illindala |
| 2014/0363391 A1 | 12/2014 | Yannopoulos et al. |
| 2015/0057580 A1 | 2/2015 | Illindala |
| 2016/0338904 A1 | 11/2016 | Lurie et al. |
| 2016/0354271 A1* | 12/2016 | Ladozhskaya-Gapeenko ............ A61H 1/003 |
| 2017/0258677 A1 | 9/2017 | Lurie |

OTHER PUBLICATIONS

Zoll Medical Corporation, "The System for High-Quality CPR", Retrieved from https://www.zoll.com/medical-technology/cpr, Accessed on Sep. 11, 2018, all pages.

Physio-Control Inc., "LUCAS CPR," retrieved from http://www.lucas-cpr.com/en/lucas_cpr/lucas_cpr, accessed on Sep. 7, 2018, all pages.

Lurie, Keith G. (2015) "The Physiology of Cardiopulmonary Resuscitation," Anesthesia & Analgesia, doi:10.1513/ANE.0000000000000926, in Ryu, et. al. "The Effect of Head Up Cardiopulmonary Resuscitation on Cerebral and Systemic Hemodynamics." Resuscitation. 2016: 102: 29-34.

Lurie, Keith G. "Mechanical Devices for cardiopulmonary resuscitation: an update," "Emergency Medicine Clinics of North America," Dec. 2002, vol. 20, Issue 4, pp. 771-784.

EP Patent Application No. 15751853.1 filed Feb. 19, 2015, Extended European Search Report dated Feb. 10, 2017, all pages.

Debaty G, et al. "Tilting for perfusion: Head-up position during cardiopulmonary resuscitation improves brain flow in a porcine model of cardiac arrest." Resuscitation. 2015: 87: 38-43.

U.S. Appl. No. 15/133,967, filed Apr. 20, 2016, Final Office Action dated Mar. 13, 2017, all pages.

Advisory Action dated Jul. 11, 2016, for U.S. Appl. No. 14/677,562, 4 pages.

Final Office Action dated May 27, 2016, for U.S. Appl. No. 14/667,562, 9 pages.

International Preliminary Report on Patentability dated Sep. 1, 2016, for International Patent Application No. PCT/US2015/016651, all pages.

International Search Report and Written Opinion dated Jul. 8, 2015 for International Patent Application No. PCT/US2015/016651, all pages.

International Search Report and Written Opinion of PCT/US2016/057366 dated Mar. 13, 2017, all pages.

Non-Final Office Action dated Aug. 26, 2016, for U.S. Appl. No. 14/996,147, 15 pages.

Non-Final Office Action dated Jan. 6, 2016, for U.S. Appl. No. 14/677,562, 33 pages.

Non-Final Office Action dated Sep. 9, 2016, for U.S. Appl. No. 14/935,262, all pages.

Non-Final Office Action dated Sep. 6, 2016, for U.S. Appl. No. 14/677,562, 12 pages.

U.S. Appl. No. 14/677,562, filed Apr. 2, 2015, Non-Final Office Action dated Jun. 13, 2017, all pages.

U.S. Appl. No. 15/133,967, filed Apr. 20, 2016, Advisory Action dated Jun. 7, 2017, all pages.

Non-Final Office Action dated Dec. 13, 2018 in related U.S. Appl. No. 15/160,492, 25 pgs.

Notice of Allowance dated Dec. 14, 2018 in related U.S. Appl. No. 14/626,770, 9 pgs.

Advisory Action dated Dec. 20, 2018 in related U.S. Appl. No. 15/265,063, 4 pgs.

Non-Final Office Action dated Jan. 28, 2019 in related U.S. Appl. No. 15/285,063, 18 pgs.

International Search Report and Written Opinion dated Feb. 11, 2019 in related PCT application No. PCT/US2018/061789, 12 pgs.

* cited by examiner

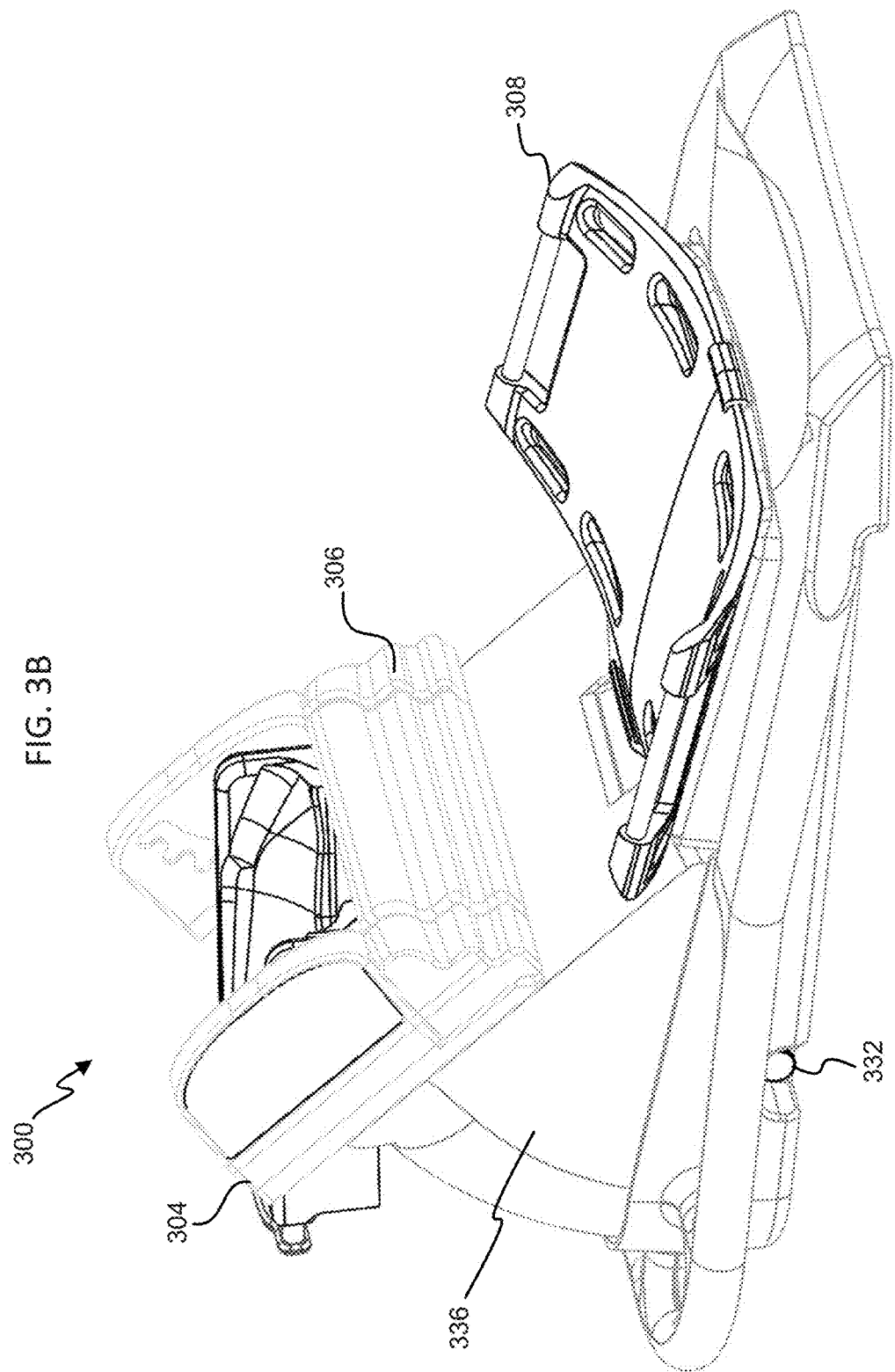

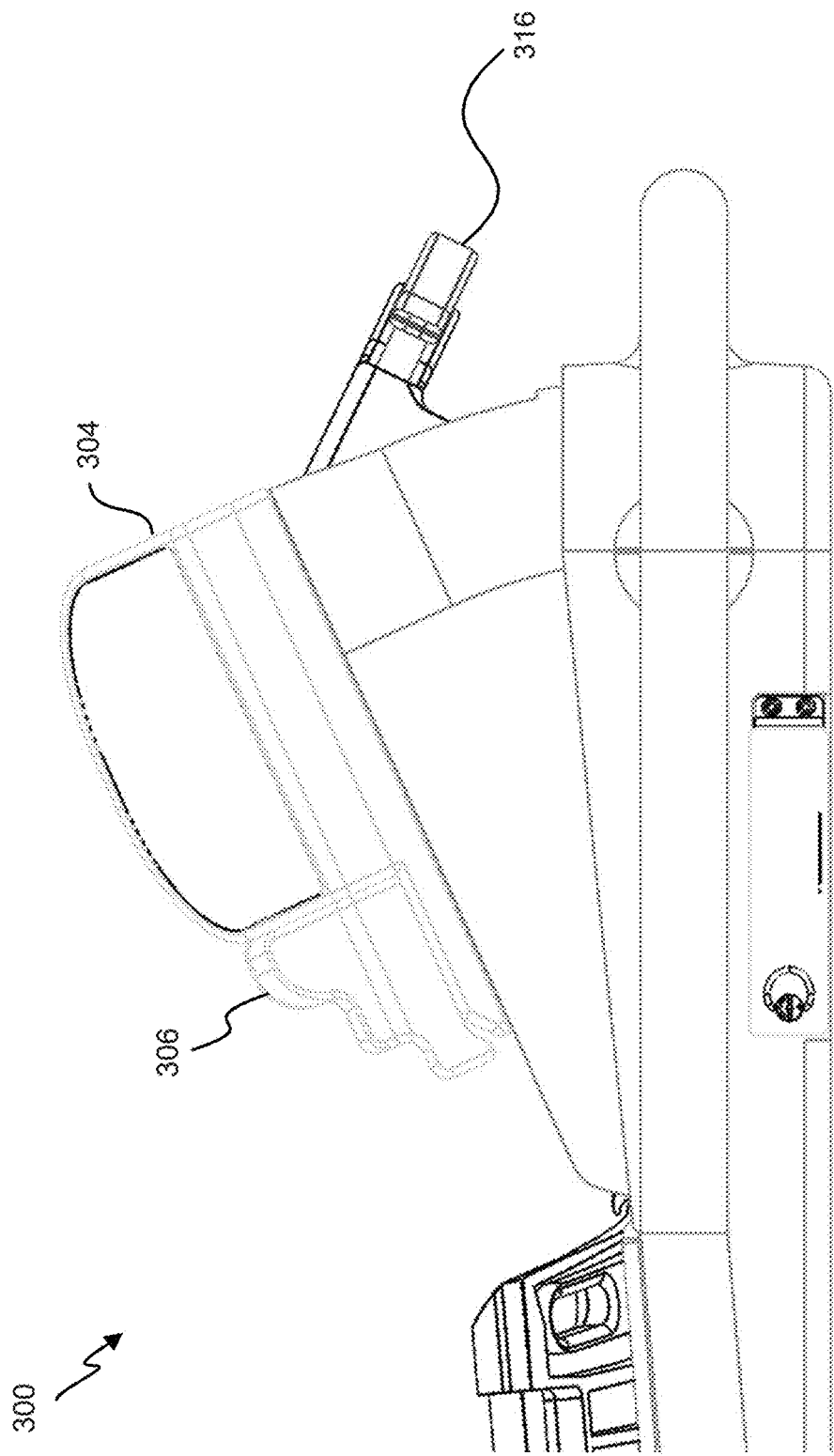

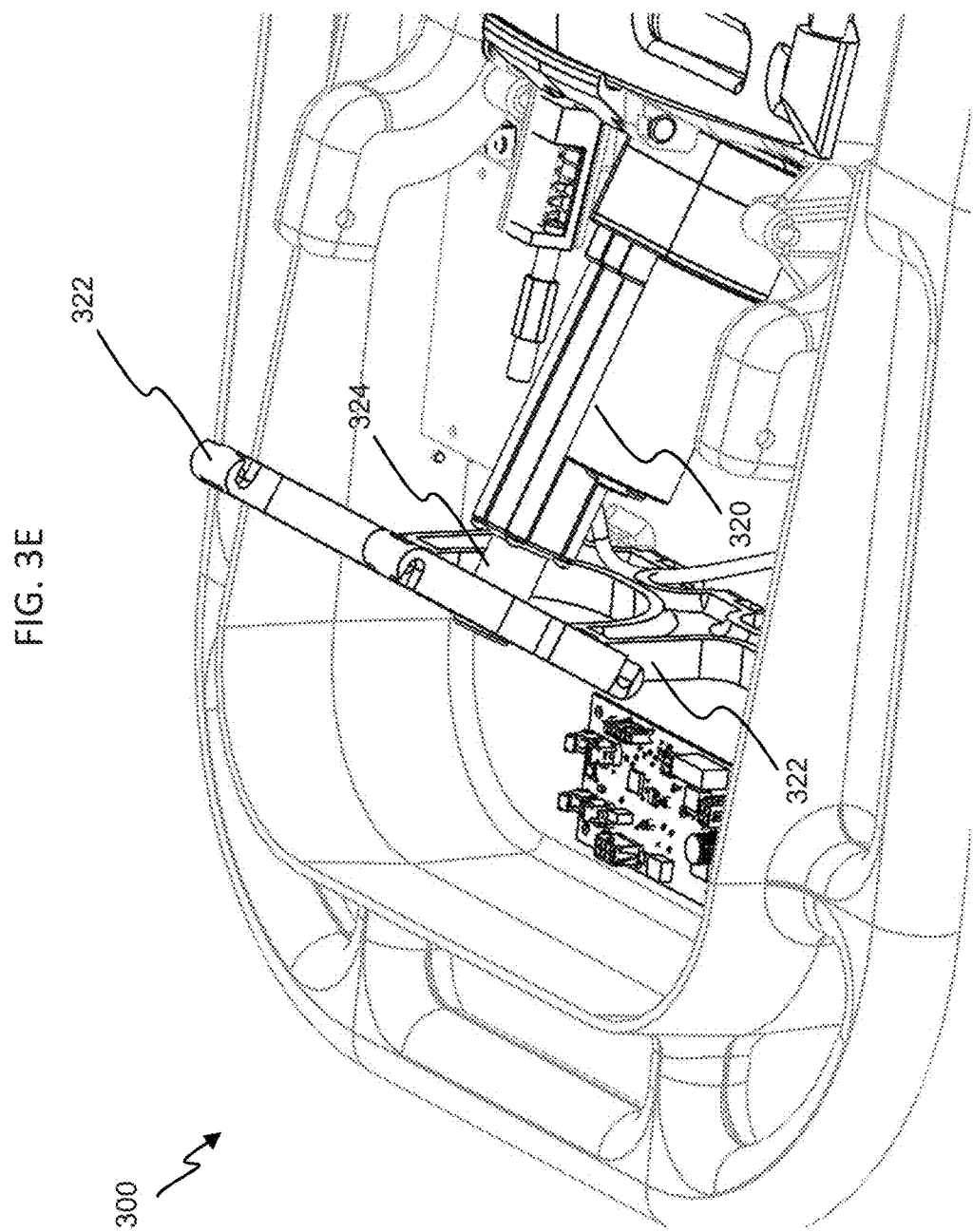

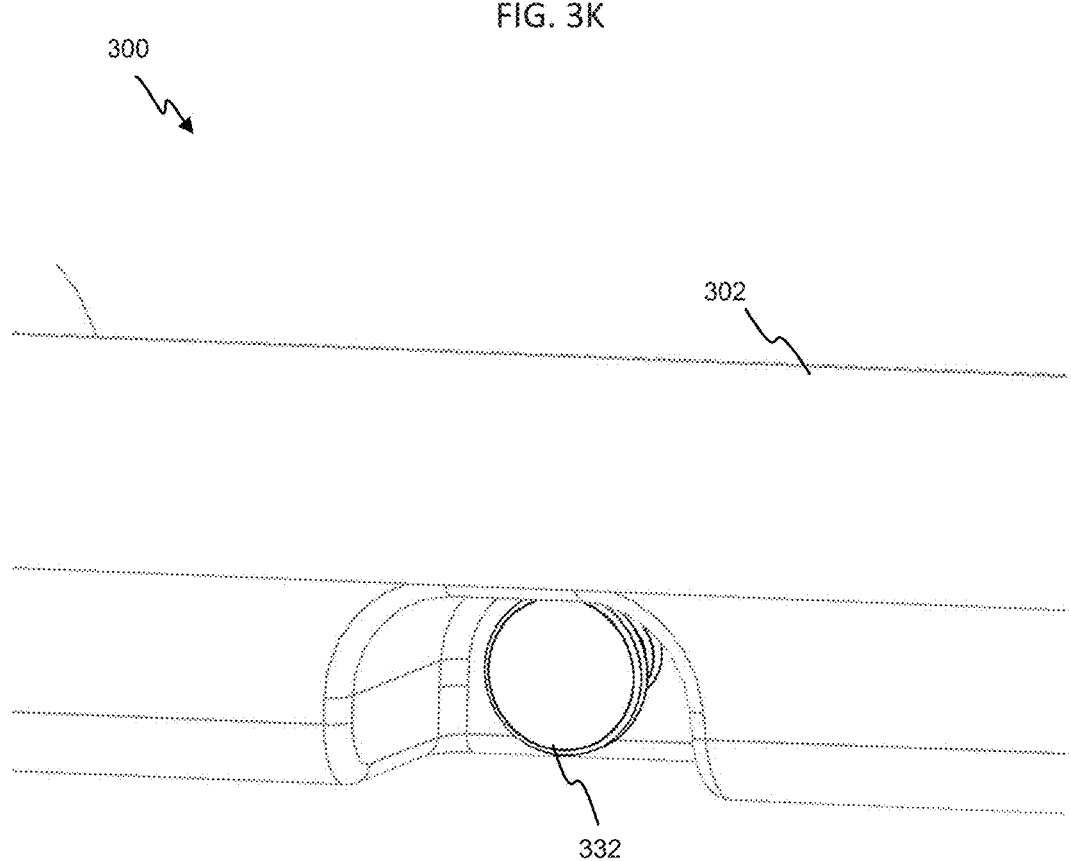

DEVICE FOR ELEVATING THE HEAD AND CHEST FOR TREATING LOW BLOOD FLOW STATES

CROSS-REFERENCES TO RELATED APPLICATIONS

This application claims priority to U.S. Provisional Application No. 62/509,469, filed May 22, 2017, the entire disclosure of which is hereby incorporated by reference for all intents and purposes.

This application is a continuation in part of U.S. application Ser. No. 15/850,827, filed Dec. 21, 2017, which is a continuation in part of U.S. application Ser. No. 15/601,494, filed May 22, 2017, which is a continuation in part of U.S. application Ser. No. 15/285,063, filed Oct. 4, 2016, which is a continuation in part of U.S. application Ser. No. 15/160,492, filed May 20, 2016, which is a continuation in part of U.S. application Ser. No. 15/133,967, filed Apr. 20, 2016, now U.S. Pat. No. 9,801,782, issued Oct. 31, 2017, which is a continuation in part of U.S. application Ser. No. 14/996,147, filed Jan. 14, 2016, now U.S. Pat. No. 9,750,661, issued Sep. 5, 2017, which is a continuation in part of U.S. application Ser. No. 14/935,262, filed Nov. 6, 2015, now U.S. Pat. No. 9,707,152, issued Jul. 18, 2017, which claims the benefit of U.S. Provisional Application No. 62/242,655, filed Oct. 16, 2015, the complete disclosures of which are hereby incorporated by reference for all intents and purposes.

U.S. application Ser. No. 14/935,262, filed Nov. 6, 2015, now U.S. Pat. No. 9,707,152, issued Jul. 18, 2017 (referenced above) is also a continuation in part of U.S. application Ser. No. 14/677,562, filed Apr. 2, 2015, which is a continuation of U.S. patent application Ser. No. 14/626,770, filed Feb. 19, 2015, which claims the benefit of U.S. Provisional Application No. 61/941,670, filed Feb. 19, 2014, U.S. Provisional Application No. 62/000,836, filed May 20, 2014, and U.S. Provisional Application No. 62/087,717, filed Dec. 4, 2014, the complete disclosures of which are hereby incorporated by reference for all intents and purposes.

BACKGROUND OF THE INVENTION

Numerous medical situations, including traumatic brain injuries, involve treatments that include elevating a patient's head and/or shoulders. Conventionally, these treatments are performed by propping the patient up at a single, set angle, such as by using a pillow, bed, or gurney. While these techniques may be generally effective at maintaining a patient in an upright or partially elevated position, they do not provide the body an opportunity to prime itself for the elevation of the head and/or chest, which may result in less than ideal blood flow to the patient's brain.

BRIEF SUMMARY OF THE INVENTION

In one aspect, a method of increasing blood flow to the head includes causing or allowing an individual's blood to circulate while the individual's heart and head are at a first elevation position and elevating the individual's heart and head to a second elevation position that is above the first elevation position. The method may also include causing or allowing the individual's blood to circulate while the individual's heart and head are at the second elevation position. The process of causing blood to circulate may continue while the individual's heart and head are elevated from the first elevation position to the second elevation position. In some cases, the first elevation position may be horizontal or when the individual is slightly bent at the waist. The rate of moving the individual from the first elevation to the second elevation position may be constant or varied, or may be paused one or more times.

In another aspect, a method of increasing blood flow to the head is provided. The method may include priming an individual's circulatory system by performing chest compressions on the individual while the individual's heart, shoulders, and head are at a first elevation position and elevating the individual's heart, shoulders, and head to a second elevation position as CPR is continued. In some cases, the first elevation position may be when the individual is flat or in a substantially horizontal position. In other cases, the first elevation position may be when the individual is bent at the waist. The second elevation position may place the individual's heart, shoulders and head above where they were when in the first elevation position.

In another aspect, a method of increasing blood flow to the head includes positioning an individual's heart, shoulders, and head to a first elevation position and priming the individual's circulatory system by performing chest compressions on the individual while the individual's heart, shoulders, and head are at the first elevation position for a period of time. The method may also include elevating the individual's heart, shoulders, and head to a second elevation position that is higher than the first elevation position after the first period of time has elapsed and performing chest compressions on the individual while the individual's heart, shoulders, and head are at the second elevation position.

In another aspect, a method of increasing blood flow to the head may include priming an individual's circulatory system while the individual's heart, shoulders, and head are at a first elevation position and elevating the individual's heart, shoulders, and head to a second elevation position. The method may also include performing chest compressions on the individual while the individual's heart, shoulders, and head are at the second elevation position. The method of increasing blood flow may also include delivering a drug, such as a vasopressor alone or in combination with a vasodilator.

In another aspect, an elevation device for use in the performance of CPR is provided. The elevation device may include a base and an upper support coupled with the base. The upper support may be configured to elevate an individual's heart, shoulders, and head relative to horizontal. The elevation device may also include an adjustment mechanism coupled with the upper support that is configured to adjust a degree of elevation of the upper support and a chest compression device. The elevation device may further include a controller coupled with the adjustment mechanism and the chest compression device. The controller may be configured to prime an individual's circulatory system by causing the chest compression device to perform chest compressions on the individual while the individual's heart, shoulders, and head are supported by the upper support at a first elevation position. The controller may be further configured to cause the adjustment mechanism to adjust the degree of elevation of the upper support to a second elevation position greater than the first elevation position after the period of time has elapsed and to cause the chest compression device to perform chest compressions on the individual while the individual's heart, shoulders, and head are at the second elevation position. In some cases, the controller may cause the degree of elevation to begin immediately from the first elevation position to the second elevation position, and may vary the rate or temporarily pause raising while continuing to perform chest compressions.

In another aspect, a method and device may be used to increase the head and thorax slowly over 1-10 minutes of CPR in order to lower ICP and improve blood flow to the brain and heart. The body is placed on the device, CPR is initiated, and then the head and thorax are elevated, in a period of time no less than 10 seconds and no longer than 12 minutes, either gradually in a linear manner, or in a non-linear manner. For example, in one embodiment the body may be placed on the device, and CPR started immediately and the head elevated to ≤30 cm above the horizontal plane and the heart to ≤15 cm above the horizontal plane over ≤10 minutes, and optimally over a 3-6 minute period of time. In another embodiment the body may be placed on the new device, CPR may be started immediately and the head elevated 10 cm and the heart to 4 cm above the horizontal plane within ≤1 minute and then the head and thorax may be elevated, in a linear or non-linear manner, up to as high as 30 cm and 15 cm, respectively, over the next 10 minutes, and more optimally over 2-6 minutes, dependent upon the method of CPR and the clinical state of the patient.

In another aspect, a method for performing CPR is provided. The method may include elevating the head, shoulders, and heart of an individual relative to a lower body of the individual using an elevation device, performing chest compressions on the individual while the head, shoulders, and heart are elevated, and detecting, using at least one sensor of the elevation device, one or both of a type of CPR performed and a duration that the type of CPR was performed.

In another aspect, a method for performing CPR includes elevating the head, shoulders, and heart of an individual relative to a lower body of the individual using an elevation device, performing chest compressions on the individual while the head, shoulders, and heart are elevated, and detecting a type of CPR performed.

In another aspect, a method for performing CPR includes elevating the head, shoulders, and heart of an individual relative to a lower body of the individual using an elevation device, performing chest compressions on the individual while the head, shoulders, and heart are elevated, and providing feedback indicating a quality of CPR performed. The feedback may be based on data from one or more pressure sensors and/or accelerometers.

In another aspect, a method for performing CPR may include elevating the head, shoulders, and heart of an individual relative to a lower body of the individual using an elevation device, performing chest compressions on the individual while the head, shoulders, and heart are elevated, and communicating a record of a type of CPR performed and a duration of CPR performed to a remote computing device.

In another aspect, a method for performing CPR may include performing chest compressions on an individual in a generally supine position using a chest compression device and elevating the head, shoulders, and heart of an individual relative to a lower body of the individual using an elevation device based on detecting that a duration of the performance of chest compressions on the individual in the generally supine position has reached a predetermined threshold. A final angle of elevation of the head, shoulders, and heart may be based on at least one physiological parameter detected by at least one sensor of the elevation device. The performance of chest compressions may be continued throughout elevation of the head, shoulders, and heart.

In another aspect, a method for performing CPR may include performing chest compressions on an individual and elevating the head, shoulders, and heart of the individual relative to a lower body of the individual using an elevation device. The method may also include detecting a change in a physiological parameter while the head, shoulders, and heart are elevated and shocking the individual using a defibrillator. A timing of the shock may be based on the change in the physiological parameter. In some embodiments, the physiological parameter may be detected based on a change in a signal of an electrocardiogram (ECG).

In another aspect, a method for performing CPR may include elevating the head, shoulders, and heart of an individual relative to a lower body of the individual using an elevation device, performing chest compressions on the individual while the head, shoulders, and heart are elevated, and lowering the head, shoulders, and heart based on detecting, using a sensor of the elevation device, that no chest compressions have been performed for a predetermined threshold.

In another aspect, a method for performing CPR may include elevating the head, shoulders, and heart of an individual relative to a lower body of the individual using an elevation device and producing, using the elevation device, an audible alarm indicating that chest compressions should be commenced based on detecting, using a sensor of the elevation device, that no chest compressions have been performed for a predetermined threshold.

In another aspect, a method for performing CPR includes performing chest compressions on the individual, regulating an intrathoracic pressure of the individual during performance of CPR, and detecting one or more gasps of the individual during performance of CPR. The method may also include recording the detected one or more gasps and alerting medical personnel of the detected one or more gasps. The method of this embodiment includes elevating the head, shoulders, and heart of the individual relative to a lower body of the individual using the elevation device. The one or more gasps may be detected while the head, shoulders, and heart are elevated relative to the lower body.

In one aspect, a system for performing CPR is provided, first in the supine and then with head and should elevation. The system may include an intrathoracic pressure regulation device configured to lower the intrathoracic pressure of an individual during CPR, a mechanism configured to detect any gasps of the individual during CPR, and an alerting mechanism configured to alert medical personnel of any detected gasps of the individual. In some embodiments, the mechanism configured to detect any gasps of the individual during CPR may be further configured to detect a gasp following a change in a position of the body of the individual during CPR.

In another aspect, a system for performing CPR, first in the supine and then with head and should elevation, may include an intrathoracic pressure regulation device configured to lower the intrathoracic pressure of an individual during CPR, a mechanism configured to sense information indicating the presence of any gasps of the individual during CPR, a memory to store the information, and a communications interface configured to transmit the information to a remote device.

In another aspect, a system for performing CPR may include an elevation device configured to elevate the head and thorax relative to the abdomen in a patient undergoing CPR. The elevation device may include at least one support surface that is configured to support an elevate the head and at least a portion of the thorax and at least one mounting support that is configured to receive and secure a chest compression device with the elevation device. The elevation device may be designed to be inserted under the patient's head and neck and thorax with minimal interruptions in CPR. The device may be designed with a rigid or semi-rigid element behind the heart to optimize compressions to the heart. In some embodiments, the elevation device further includes a stowable shelf that is configured to extend from a stowed position outward from the elevation device to an extended position in which at least a portion of the stowable shelf protrudes from a body of the elevation device at a height of between about 2 inches and 4 inches relative to a bottom edge of the elevation device. The stowable shelf may be configured to support a rescuer when in the extended position such that the rescuer is elevated above the ground for optimal support and positioning over the individual.

BRIEF DESCRIPTION OF THE DRAWINGS

FIG. 3B depicts the elevation device of FIG. 3A in an elevated position.

FIG. 3D depicts the locking handle of the elevation device of FIG. 3A.

FIG. 3E depict a linear actuator of the elevation device of FIG. 3A in an elevated position.

FIG. 3I depicts a latch of the elevation device of FIG. 3A.

FIG. 3K depicts a release knob of the elevation device of FIG. 3A.

DETAILED DESCRIPTION OF THE INVENTION

Figure 1A:
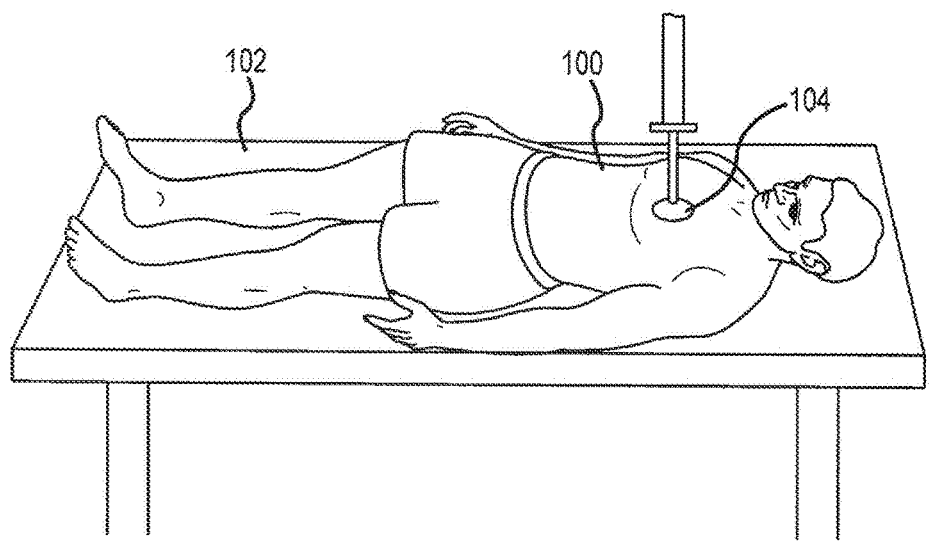
FIG. 1A is a schematic of a patient receiving CPR in a supine configuration according to embodiments.

Embodiments of the present invention are directed to devices and techniques for elevating the head and chest for treating low blood flow states. The devices and techniques described herein may be used to treat and/or in conjunction with other treatments for any number of low blood flow states, such as traumatic brain injury conditions. The techniques described herein involve elevating a patient's head and/or chest in a slow and controlled manner, continuously to a final height and/or involving stopping elevation of the head and/or chest at a lower, intermediate height for a period of time to allow the body to prime itself to push blood uphill effectively prior to further elevating the head and/or chest to the final height.

In some embodiments, the techniques and devices described herein may be used, for example, in the performance of head up (HUP) cardiopulmonary resuscitation (CPR), in which the head and thorax are elevated while performing CPR. HUP CPR has been shown to be superior to flat CPR in terms of improving cerebral and coronary perfusion and perfusion pressures. However, HUP CPR can be dangerous if 1) the head is elevated before starting CPR (there is a need to prime the system), 2) elevation of the head occurs too quickly as filling/priming pressures bottom out, 3) there is too much elevation of the head, 4) the head is elevated with the feet down for prolonged periods of time, or 5) the head/thorax are elevated during CPR without circulatory enhancers (e.g., intrathoracic pressure regulation, such as that provided by an impedance threshold device (ITD)). Without an adequate mean arterial pressure (MAP) or adequate flow elevation of the head during CPR is harmful.

With HUP CPR, elevation of the head too rapidly is suboptimal and potentially harmful, especially since forward flow is inherently limited due to the non-invasive external chest compressions and release that drive blood flow and blood pressure. The forward flow on the arterial side must overcome the effects of gravity on the arterial side in order for HUP CPR to be of benefit. Since conventional standard CPR is so inefficient, it is difficult, if not impossible, to derive a benefit from HUP CPR with just standard CPR alone; there is a mismatch between the effects of gravity on the arterial pressure versus the fixed and limited forward blood flow generated with standard CPR alone. This is relevant as some methods of CPR generate more flow and pressures than others, and the greater the forward flow, the more one can take advantage of HUP CPR.

Recent discoveries have shown that elevation of the head and thorax improves blood flow to the heart and brain in at least three unique ways. First venous blood is rapidly drained by gravity from the brain. Second, the simultaneous concussion of the brain by high arterial and venous pressure waves is reduced as the venous pressures (and thus the ICP) are reduced by gravity. Third, cardiopulmonary circulation is improved as elevation of the lungs results in a gradient of blood volume within the lungs, with greater congestion in the lower portions and less congestion in the upper portions (physiology similar to a patient with heart failure who feels better sitting up). Elevation of the head and thorax during CPR also appears to reduce the likelihood of brain edema after cardiac arrest. These unique benefits are attributable to the HUP CPR approach.

A discovery that is central to the present invention is that during HUP CPR it is necessary to prime the pump (circulatory system) at a lower height and/or lesser angle for a period of time, generally between 1-5 minutes for the system to be able to function optimally and to be able to get the full benefit of HUP CPR. One way to conceptualize this is to think about other therapies which benefit from a more graduate delivery: for example certain drugs. For example, if there is a drug that is therapeutic but can cause low blood pressure when administered too rapidly, then the drug may be administered more slowly by IV drip instead of as a bolus.

Embodiments of the present invention relate to systems and methods for performing HUP CPR that reduce the risk associated with HUP CPR and provide enhanced benefits by elevating an individual's heart, shoulders, and head in a gradual manner, thereby priming the body for HUP CPR. In the present invention, the elevation of the head and thorax may be done in a sequence by 1) elevating the head and thorax over two or more sequential elevation steps and/or 2) elevating the head and thorax over a more prolonged period of time from the start of the elevation to the final height. Slowly raising the head and thorax during HUP CPR, in a sequential and graduated manner (priming the body), rather than going straight to the highest angle, is best for this dynamic physiological system, as such sequential elevation allows the circulatory system to adjust to the change in elevation of the head and thorax. Priming the individual may involve performing chest compressions for a period of time prior to elevating the individual to a final elevation position. In some embodiments, the individual may be primed by performing CPR for a period of time (between about 30 seconds and 10 minutes, more commonly between about 2 minutes and 8 minutes, and more commonly between about 3 minutes and 6 minutes) while the individual is in a flat, supine position (or nearly supine, such as with the head and/or heart elevated slightly to an angle of less than about 5 degrees relative to horizontal) prior to elevating the individual to an intermediate and/or final height. In some embodiments where the individual has been primed flat, an additional priming step may be performed at an intermediate elevation position prior to elevating the individual to the final/highest elevation position. In other embodiments, the individual may be primed by first elevating the individual's head and heart to one or more intermediate elevation positions (i.e. between about 10 and 25 degrees) and then performing chest compressions for a period of time prior to elevating the individual's heart and head to a final elevation position (i.e. between 20 and 45 degrees). In some embodiments, incrementally priming the individual from a flat or generally flat position up to a final elevation position of between about 30 and 45 degrees may be ideal, while in other embodiments, an individual may be promptly elevated to a position of between about 8 and 15 degrees (commonly around 10 degrees) before gradually, over a period of between about 20 seconds to 10 minutes, priming the individual up to the final elevation position. The chest compressions may be continued during the elevation adjustment periods after each priming step.

In particular, embodiments of the present invention involve HUP CPR in which elevation of the head and thorax is performed in a deliberate, systematic, and sequential manner to optimize the advantages of HUP CPR and minimize the potential for harm. For example, elevation of the head and thorax during HUP CPR is done in at least two sequential steps. The first step may involve elevating the head and heart between 10-25° for a given period of time (with a minimal time duration of 30 seconds and a maximum time duration of 10 minutes, more commonly between 2 minutes and 8 minutes, and optimally between about 3 minutes and 6 minutes during ACD+ITD CPR), with the second sequential step involving further elevation of the head and thorax to between 20-45° thereafter. The elevation time may be controlled such that the elevation of the individual's head and torso does not exceed a particular rate. As just one example, the elevation speed may be maintained at a rate of not faster than 1° over each 0.3 second period. Thus, for example, elevation of the head and thorax from 0° (in alignment with a horizontal plane) to 30° would take place over at least 9 seconds. The preferable lift speed is between about 1°/0.15 seconds and 1°/3 seconds, oftentimes around about 1°/1.0 second. The lift speed may be linear and/or non-linear throughout each elevation step.

The duration of time at any given HUP elevation position before progressing to the next elevation could be set empirically or guided and/or driven by a physiological parameter. For example, in some embodiments, the duration of time at a particular HUP elevation position may be preset to an average value based on empirical results, such as spending between about 30 seconds to about 10 minutes (more commonly between about 2 minutes and 8 minutes and even more commonly between about 3 minutes and 6 minutes) at a particular elevation position before elevating or further elevating the individual's head and upper torso. In other embodiments, physiological parameters, such as blood flow, blood pressure, end tidal $CO_2$, cerebral oximetry, and/or other sensed physiological measures that correlate directly or indirectly with cardio-pulmonary circulation and perfusion may be monitored. Upon the parameter(s) reaching a particular level, the individual may be automatically elevated and/or further elevated. In some embodiments, the regulations of the HUP CPR could be incorporated into a closed-loop design such that an elevation device may be preprogrammed to properly prime and/or elevate the individual sequentially based on the empirical duration of time and/or based on physiological measurements.

As noted above, other embodiments of sequential elevation HUP CPR may be performed by slowly and continuously raising the individual's heart, shoulders, and head from a starting elevation position to a final elevation position. For example, a starting elevation position may include the individual being positioned in a generally flat, supine position (with the head elevated less than 5° relative to horizontal). The individual's head, shoulders, and heart may be slowly raised (linearly and/or non-linearly) from the starting elevation position to a position where the head is elevated between about 20 and 45 degrees relative to horizontal (an absolute elevation of the heart by about 5-10 cm and an absolute elevation of the head by about 15-25 cm, although these ranges may vary based on the age, size, and/or physiology of a specific individual) over a period of between about 30 seconds and 10 minutes, more commonly between 2 minutes and 8 minutes, and optimally between about 3 minutes and 6 minutes, while CPR is performed. For example, the head, shoulders, and heart may be raised at a rate of between about 2.25°/second and about 1.5°/minute. In other embodiments, an individual may be quickly raised to a starting elevation position of between about 8-15 degrees before slowly elevating the head, shoulders, and heart to a final elevation position over a period of between about 30 seconds and 10 minutes, more commonly between 2 minutes and 8 minutes, and optimally between about 3 minutes and 6 minutes, while CPR is performed.

Figure 1B:
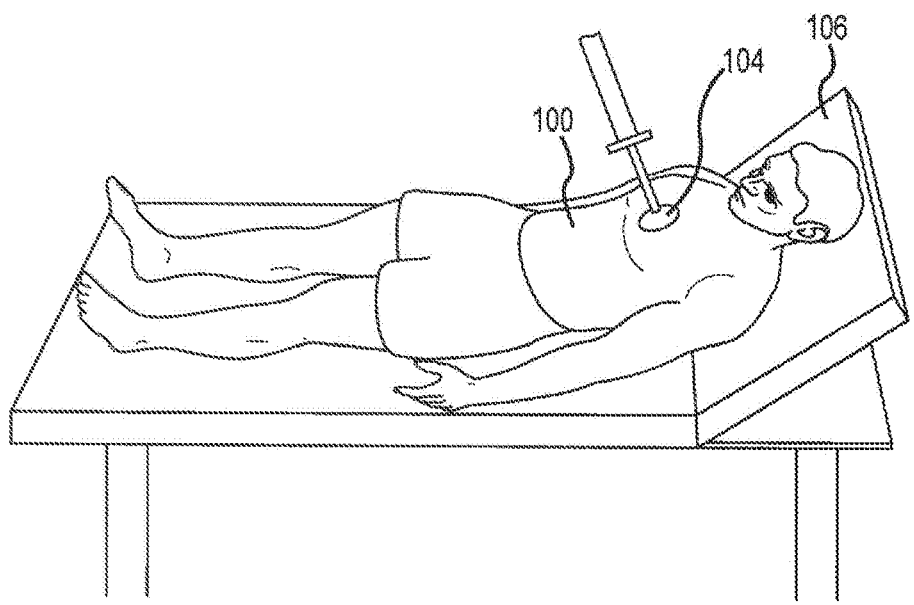
FIG. 1B is a schematic of a patient receiving CPR in a head and thorax up configuration according to embodiments.

Turning now to FIG. 1A, a demonstration of the standard supine (SUP) CPR technique is shown. Here, a patient 100 is positioned horizontally on a flat or substantially flat surface 102 while CPR is performed. CPR may be performed by hand and/or with the use of an automated CPR device and/or ACD+CPR device 104. In contrast, a HUP CPR technique is shown in FIG. 1B. Here, the patient 100 has his head and thorax elevated above the rest of his body, notably the lower body. The elevation may be provided by one or more wedges or angled surfaces 106 placed under the patient's head and/or thorax, which support the upper body of the patient 100 in a position where both the head and thorax are elevated, with the head being elevated above the thorax. HUP CPR may be performed with conventional standard CPR alone, with ACD alone, with the ITD alone, with the ITD in combination with conventional standard CPR alone, and/or with ACD+ITD together. Such methods regulate and better control intrathoracic pressure, causing a greater negative intrathoracic pressure during CPR when compared with conventional manual CPR. In some embodiments, HUP CPR may also be performed in conjunction with extracorporeal membrane oxygenation (ECMO). HUP CPR can also be performed with a number of different automated CPR devices, including those that compress the chest and allow for passive or active recoil, and those that also circumferentially compress the chest, with or without active chest recoil.

Figure 2A:
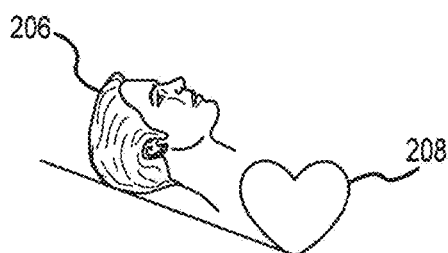
FIG. 2A is a schematic showing a configuration of HUP CPR according to embodiments.
Figure 2B:
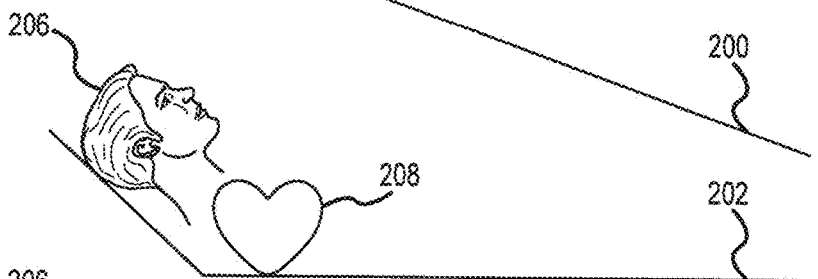
FIG. 2B is a schematic showing a configuration of HUP CPR according to embodiments.
Figure 2C:
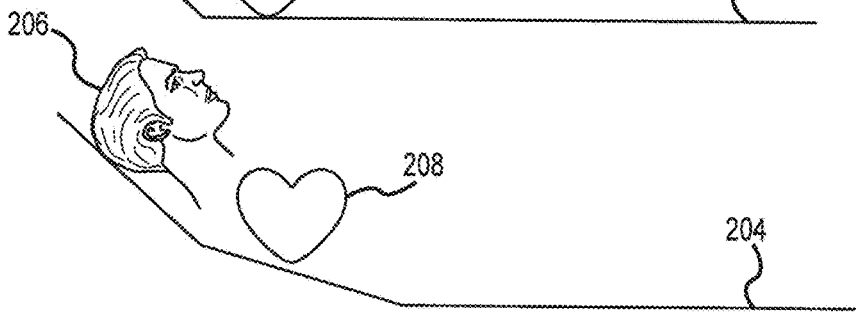
FIG. 2C is a schematic showing a configuration of HUP CPR according to embodiments.

FIGS. 2A-2C demonstrate various set ups for HUP CPR as disclosed herein. Configuration 200 in FIG. 2A shows a user's entire body being elevated upward at a constant angle. As noted above, such a configuration may result in a reduction of coronary and cerebral perfusion during a prolonged resuscitation effort since blood will tend to pool in the abdomen and lower extremities over time due to gravity. This reduces the amount of effective circulating blood volume and as a result blood flow to the heart and brain decrease over the duration of the CPR effort. Thus, configuration 200 is not ideal for administration of CPR over longer periods, such as those approaching average resuscitation effort durations. Configuration 202 in FIG. 2B shows only the patient's head 206 being elevated, with the heart and thorax 208 being substantially horizontal during CPR. Without an elevated thorax 208, however, systolic blood pressures and coronary perfusion pressures are lower as lungs are more congested with blood when the thorax is supine or flat. This, in turn, increases pulmonary vascular resistance and decreases the flow of blood from the right side of the heart to the left side of the heart when compared to CPR in configuration 204. Configuration 204 in FIG. 2C shows both the head 206 and heart/thorax 208 of the patient elevated, with the head 206 being elevated to a greater height than that heart/thorax 208. In some embodiments, such as those where a method of CPR is performed that generates sufficient forward flow (such as ACD+ITD CPR) this elevation may be achieved by elevating the head 206 and heart/thorax 208 at a constant angle from the waist to the head. Such elevation results in lower right-atrial pressures while increasing cerebral perfusion pressure, cerebral output, and systolic blood pressure compared to CPR administered to an individual in the supine position, and may also preserve a central blood volume and lower pulmonary vascular resistance.

The type of CPR being performed on the elevated patient may vary. Examples of CPR techniques that may be used include manual chest compression, chest compressions using an assist device, either automated or manually, ACD CPR, a load-distributing band, standard CPR, stutter CPR, and the like. Such processes and techniques are described in U.S. Pat. Pub. No. 2011/0201979 and U.S. Pat. Nos. 5,454,779 and 5,645,522, all incorporated herein by reference. Further, various sensors may be used in combination with one or more controllers to sense physiological parameters as well as the manner in which CPR is being performed. The controller may be used to vary the manner of CPR performance, adjust the angle of inclination, the speed of head and thorax rise and descent, provide feedback to the rescuer, and the like. Further, a compression device could be simultaneously applied to the lower extremities or abdomen to squeeze venous blood back into the upper body, thereby augmenting blood flow back to the heart. Further, a compression-decompression band could be applied to the abdomen that compresses the abdomen only when the head and thorax are elevated either continuously or in a pulsatile manner, in synchrony or asynchronously to the compression and decompression of the chest. Further, a rigid or semi-rigid cushion could be simultaneously inserted under the thorax at the level of the heart to elevate the heart and provide greater back support during each compression.

Additionally, a number of other procedures may be performed while CPR is being performed on the patient in the torso-elevated state. For example, intrathoracic pressure regulation may be performed, which involves actively drawing air out of the lungs and/or preventing air from entering the lungs to control a patient's intrathoracic pressure, such as by using ACD+CPR, an impedance threshold device, a load distributing band, a ventilator, and the like. One such procedure is to periodically prevent or impede the flow in respiratory gases into the lungs. This may be done by using a threshold valve, sometimes also referred to as an impedance threshold device (ITD) that is configured to open once a certain negative intrathoracic pressure is reached. The invention may utilize any of the threshold valves or procedures using such valves that are described in U.S. Pat. Nos. 5,551,420; 5,692,498; 5,730,122; 6,029,667; 6,062,219; 6,810,257; 6,234,916; 6,224,562; 6,526,973; 6,604,523; 6,986,349; and 7,204,251, the complete disclosures of which are herein incorporated by reference.

Another such procedure is to manipulate the intrathoracic pressure in other ways, such as by using a ventilator or other device to actively withdraw gases from the lungs. Such techniques as well as equipment and devices for regulating respirator gases are described in U.S. Pat. Pub. No. 2010/0031961, incorporated herein by reference. Such techniques as well as equipment and devices are also described in U.S. patent application Ser. No. 11/034,996 and Ser. No. 10/796,875, and also U.S. Pat. Nos. 5,730,122; 6,029,667; 7,082,945; 7,310,649; 7,195,012; and 7,195,013, the complete disclosures of which are herein incorporated by reference.

In some embodiments, the angle and/or height of the head and/or heart may be dependent on a type of CPR performed and/or a type of intrathoracic pressure regulation performed. For example, when CPR is performed with a device or device combination capable of providing more circulation during CPR, the head may be elevated higher, for example 10-30 cm above the horizontal plane (10-45 degrees) such as with ACD+ITD CPR. When CPR is performed with less efficient means, such as manual conventional standard CPR, then the head may be elevated less, for example 10-20 cm or 10 to 20 degrees.

In some embodiments, an elevation device, such as those described in U.S. application Ser. No. 15/850,827 and U.S. application Ser. No. 15/601,494 (previously incorporated by reference), may be programmed to perform sequential elevation HUP CPR and/or used in the treatment of other low blood flow conditions as described herein. For example, an elevation device may include a base and an upper support coupled with the base. The upper support may be configured to elevate an individual's heart, shoulders, and head relative to horizontal. In some embodiments, the upper support may include a single support surface that is configured to elevate the heart and head at a single angle, such as by bending the patient at or near the waist. In other embodiments, the upper support may include multiple support surfaces that may elevate the heart and head at different angles. The upper support may include an adjustment mechanism that is configured to adjust a degree of elevation of the upper support. For example, a motor or other actuator may be used to drive the angular and/or height adjustment of the upper support relative to the base. In some embodiments, a controller may be coupled with the adjustment mechanism and may be used to control the elevation of the upper support. For example, the controller may execute instructions that determine when and to what degree the adjustment mechanism adjusts the elevation position of the upper support. This may be based off of timing instructions that are derived from empirical studies and/or the elevation may be controlled based on one or more physiological parameters measured by one or more sensors that are in communication with the controller. For example, blood flow sensors, blood pressure sensors, end tidal $CO_2$ sensors, cerebral oximetry sensors, and/or sensors that monitor other physiological parameters that correlate directly or indirectly with cardio-pulmonary circulation and perfusion may be connected to the controller such that the controller may make adjustments in elevation degree and/or timing based on the sensed parameters.

The elevation device may also include a chest compression device, such as an automated chest compression device. In some embodiments, the chest compression device may be a load distributing band, a piston-based chest compression device, a combination of a load distributing band and an active decompression device, and/or other automated and/or manually actuated chest compression device. In some embodiments, the chest compression device may be configured to actively decompress the individual's chest between each compression such that the chest compression device may be used in the performance of ACD-CPR. In some embodiments, the controller may be coupled with the chest compression device such that the controller may control a rate and/or timing of the chest compressions being delivered to an individual according to the sequential elevation procedures described herein. The compression depth, decompression depth, rate of compression and decompression, and/or duty cycle may be varied based on a particular individual and/or based on measurements from the physiological sensors. In some embodiments, the CPR may be delivered continuously or with pauses for a positive pressure breath and/or with 3-5 short and intentional pauses at the start of CPR to allow for reperfusion injury protection. In each of these examples, the head and thorax can also be lowered if clinically required, in some cases rapidly in less than 6 seconds.

Figure 3A:
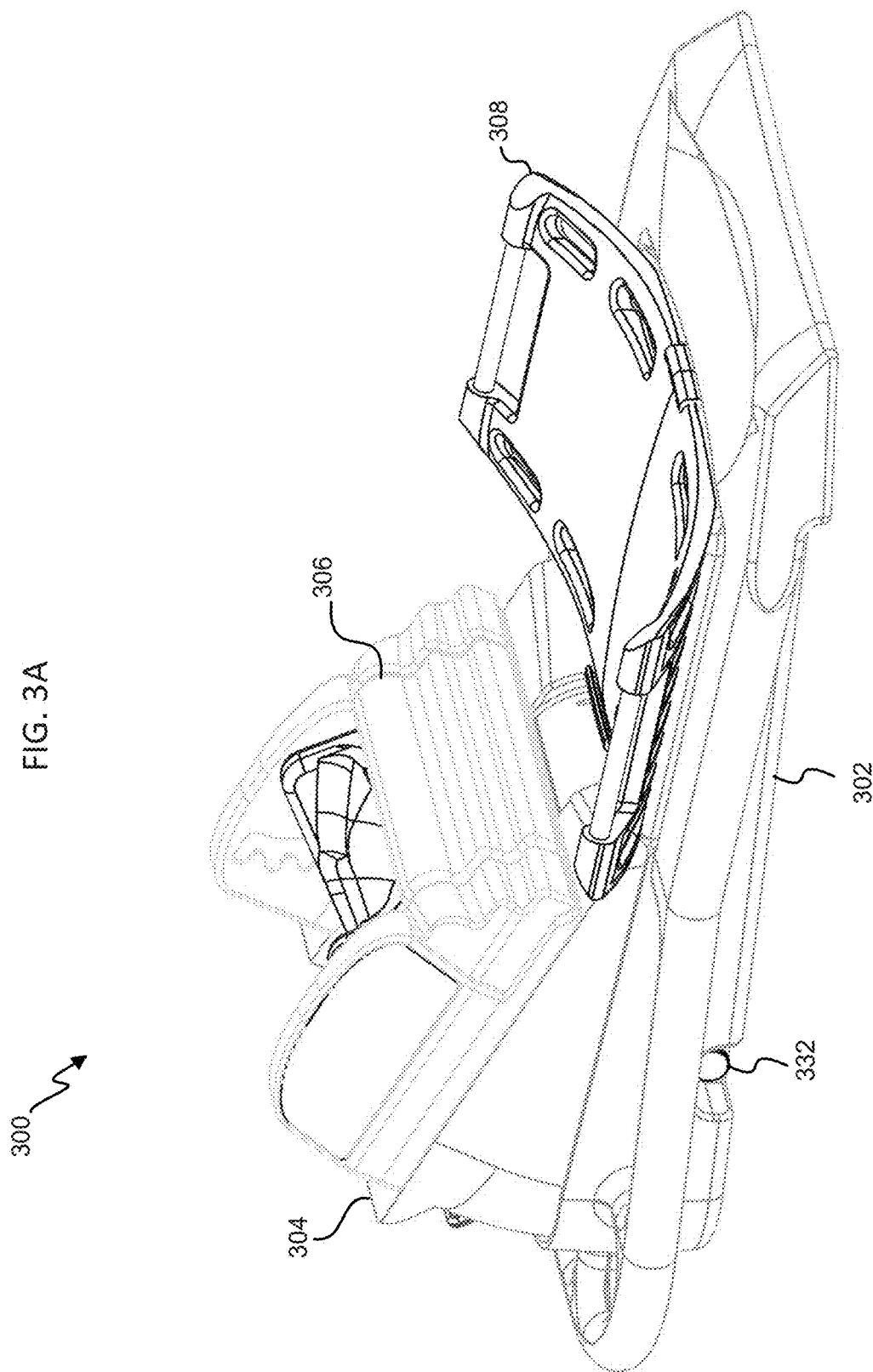
FIG. 3A depicts an elevation device in a lowered position according to embodiments.
Figure 3C:
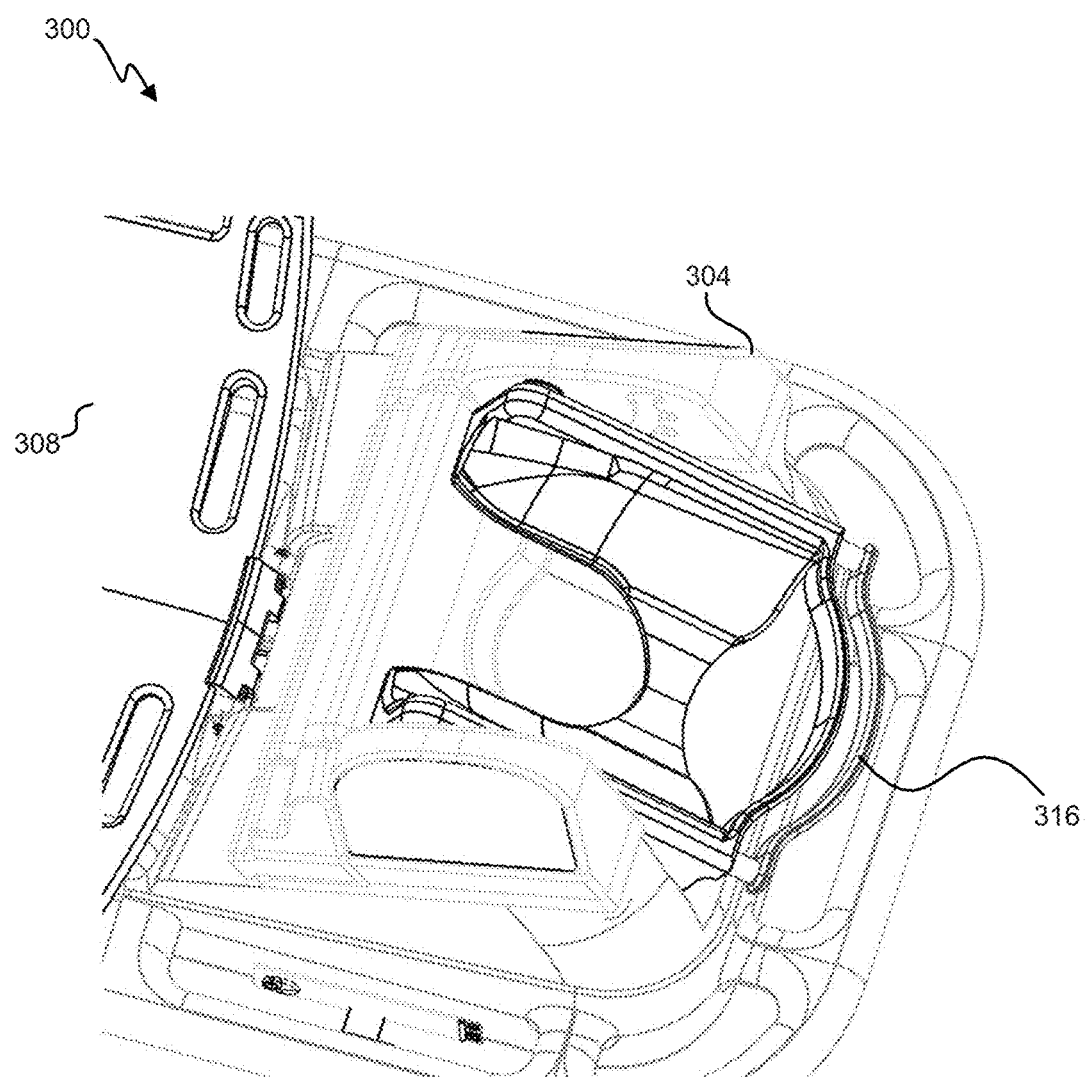
FIG. 3C depicts a locking handle of the elevation device of FIG. 3A.

FIGS. 3A-3L depict an example of an elevation device 300, which may be similar to other elevation devices described herein. This device is designed to be placed under the patient, for example, as soon as a cardiac arrest is diagnosed. It has a low profile designed to slip under the patient's body rapidly and easily. For example, FIG. 3A shows that elevation device 300 may include a base 302 that supports and is pivotally or otherwise operably coupled with an upper support 304. Upper support 304 may include a neck pad or neck support 306, as well as areas configured to receive a patient's upper back, shoulders, neck, and/or head. An elevation mechanism may be configured to adjust the height and/or angle of the upper support 304 throughout the entire ranges of 0° and 45° relative to the horizontal plane and between about 5 cm and 45 cm above the horizontal plane. In some embodiments, the upper support 304 may be configured to elevate the middle of the patient's head to a height that is between about 2 and 42 cm above a middle of the heart. In some embodiments, an angle between the middle of the patient's head and a middle of the heart is between about 10 and 40 degrees relative to horizontal.

A user may be positioned on the elevation device 300 with his neck positioned on the neck support 306. In some embodiments, the neck support 306 may contact the individual's spine at a location near the C7 and C8 vertebrae. This position may help maintain the individual in the sniffing position, to help enable optimum ventilation of the individual. In some embodiments, the individual may be aligned on the elevation device 300 by positioning his nipples just above a center line of the back plate 308. The chest compression device is coupled with the back plate 308 such that the chest compression device is in alignment with the individual's sternum at a generally orthogonal angle to ensure that the chest compressions are delivered at a proper angle and with proper force. In some embodiments, the alignment of the chest compression device may be achieved may configuring the chest compression device to pivot and/or otherwise adjust angularly to align the chest compression device at an angle substantially orthogonal to the sternum.

As shown in FIG. 3A, elevation device 300 is in a lowered position, with the upper support 304 being configured to maintain the patient's head at a position that is slightly elevated relative to the heart, which is supported by back plate 308. In the lowered position, a head-receiving portion of the upper support 304 (which is designed to maintain the patient in the sniffing position and extends downward from a top surface of the upper support 304) maintains the base of the head at a generally horizontal level (within about 5 degrees) when in a fully lowered position. The upper support 304 may be raised as shown in FIG. 3B to elevate the patient's head, shoulders, and/or heart, which the head being supported at heights of between about 5 cm and 45 cm relative to a horizontal support surface on which the base 302 is supported. Upper support 304 may be configured to be adjustable such that the upper support 304 may slide along a longitudinal axis of base 302 to accommodate patients of different sizes as well as to accommodate movement of a patient associated with the elevation of the head by upper support 304. Without such sliding ability, a patient's upper body has a tendency to curl forward on the elevation device 300 as the patient's upper body is elevated. As shown in FIG. 3B, the upper support 304, including neck support 306, are extended away from the back plate 308 when the upper support 304 is elevated. In some embodiments, this sliding movement may be locked once an individual is positioned on the elevated upper support 304. In some embodiments, the upper support 304 may include one or more springs that may bias the upper support 304 toward the torso. This allows the upper support 304 to slide in a controlled manner when the individual's body shifts during the elevation process. In some embodiments, the one or more springs may have a total spring force of between about 10 lb. and about 50 lbs., more commonly between about 25 lb. and about 30 lb. Such force allows the upper support 304 to maintain a proper position, yet can provide some give as the head and upper torso are elevated. Further, the elevation device may include a slide mechanism such that with elevation of the head and neck the portion of elevation device behind the head and shoulder elongates. For example, the slide mechanism may include roller bearings that are mounted on a track that allows the upper support 304 to slide to accommodate patients of different sizes as well as to handle shifting of the body during elevation, which helps to maintain the neck in the sniffing position. In some embodiments, such as those shown in FIGS. 3C and 3D, a locking handle 316 is provided that allows medical personnel to adjust a lateral position of the upper support 304 relative to the base 302. To actuate the handle 324, a user must apply force to push a distal portion 326 of the handle 324 toward a fixed, proximal portion 328 of the handle 316. This action pushes a locking member (not shown) into a free space of a ratchet mechanism, allowing the user to adjust the lateral position of the upper support 304. Once released, the locking member may enter a tooth of the ratchet to set a position of the upper support 304 based on a size of the user. The upper support 304 may then only slide in small amounts to handle the shifting of the patient throughout the elevation process.

Figure 3F:
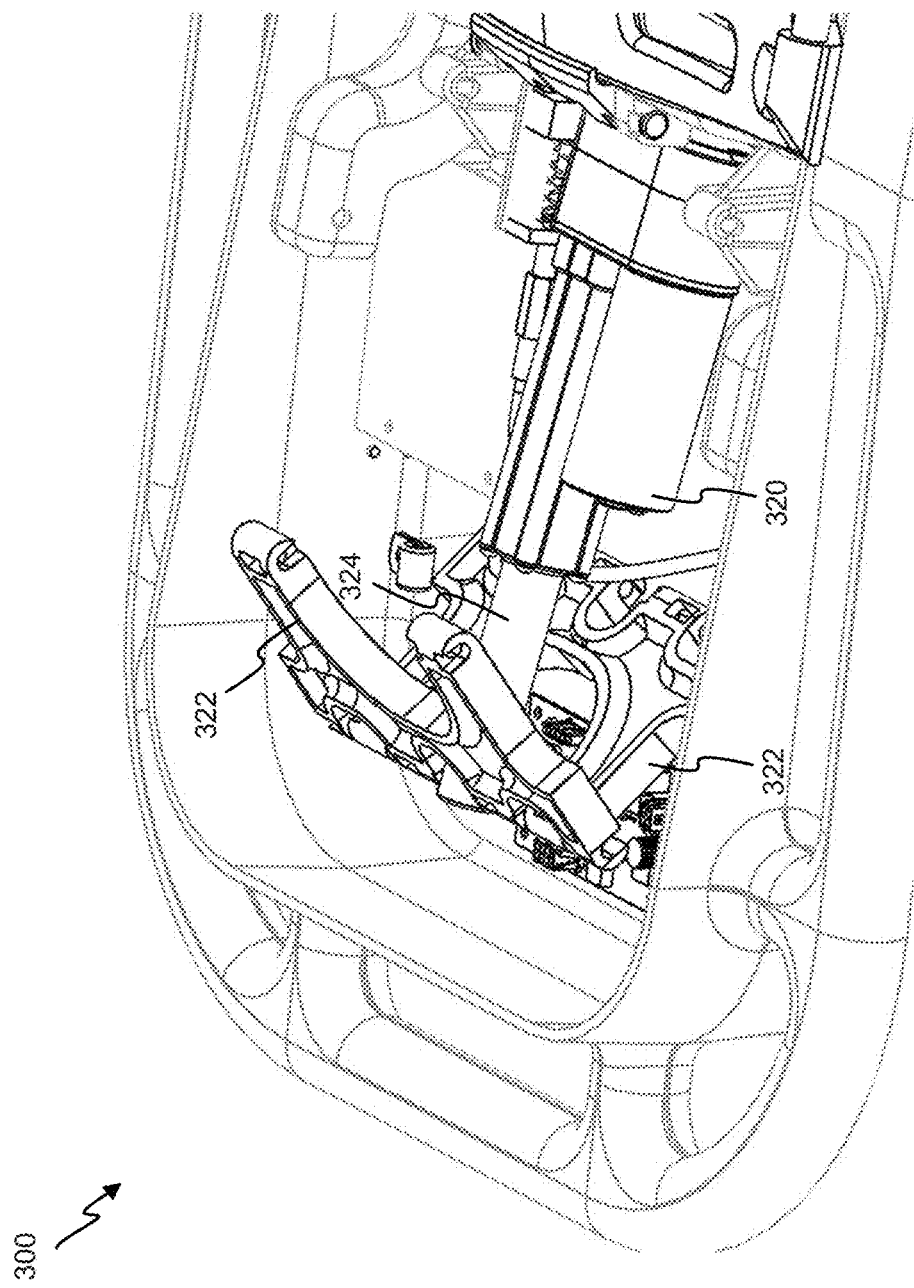
FIG. 3F depict the linear actuator of the elevation device of FIG. 3A in a lowered position.

FIGS. 3E and 3F depict a linear actuator 320 that is used to raise and lower the upper support 304. Linear actuator 320 is coupled at a joint formed between two or more support members 322. Support members 322 are coupled between the base 302 and a bottom surface of the upper support 304 such that top support member(s) 322 is coupled with the upper support 304 and the bottom support member(s) 322 is coupled with the base 302. As linear actuator 320 is operated, a rod 324 of the linear actuator 320 shortens to draw the joint of the support members 322 toward the back plate 308, which causes an angled between the top and bottom supper members 322 to increase, such as shown in FIG. 3E, forcing the upper support 304 upward to elevate a patient's upper body. When operated in reverse, the rod 324 of linear actuator 320 extends, pushing on the joint to decrease the angle between the top and bottom support members 322 as shown in FIG. 3F, thereby lowering the upper support 304. It will be appreciated that the direction of operation of the linear actuator 320 and support members 322 may be reversed in some embodiments such that lengthening rod 324 causes elevation of the upper support 304 and shortening of rod 324 causes the lowering of the upper support 304. While shown here with a linear actuator 320 and support member 322 elevation mechanism, it will be appreciated that elevation device 300 may additionally or alternatively include other elevation mechanisms, such as threaded rods, lead screws, pneumatic and/or hydraulic actuators, motor driven telescopic rods, other elevation mechanisms, and/or combinations thereof.

Turning back to FIGS. 3A and 3B, the back plate 308 may be sized and shaped to receive a portion of the patient's back, just behind the heart and may be configured to couple with a chest compression device (not shown). Examples of CPR assist devices that could be used with the elevation device (either in the current state or a modified state) include the Lucas device, sold by Physio-Control, Inc. and described in U.S. Pat. No. 7,569,021, the entire contents of which is hereby incorporated by reference, the Defibtech Lifeline ARM—Hands-Free CPR Device, sold by Defibtech, the Thumper mechanical CPR device, sold by Michigan Instruments, automated CPR devices by Zoll, such as the AutoPulse, as also described in U.S. Pat. No. 7,056,296, the entire contents of which is hereby incorporated by reference, the Weil Mini Chest Compressor Device, such as described in U.S. Pat. No. 7,060,041 (Weil Institute), and the like. Chest compression devices used in accordance with the present invention may be configured to compress and/or actively decompress the chest.

In some embodiments, the back plate 308 may have a curved profile that may provide some flexibility to the back plate 308. This flexibility helps when the elevation device 300 is used in conjunction with a chest compression device, as the flexibility ensures that the right amount force applied to the patient's chest. For example, a central portion of the back plate 308 may flex in the presence of excessive force, thereby absorbing some of the force. For example, as a plunger of a chest compression device is pressed into the patient's chest, some force is transmitted through the patient to the back plate 308. The back plate 308 may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing back plate 308, rather than the ribs or other body structures, absorbs a significant portion of the excess force. Such a design is particularly useful when the elevation device is used in conjunction with a chest compression device such as the Lucas device, sold by Physio-Control, Inc. and/or the Zoll AutoPulse.

Figure 3G:
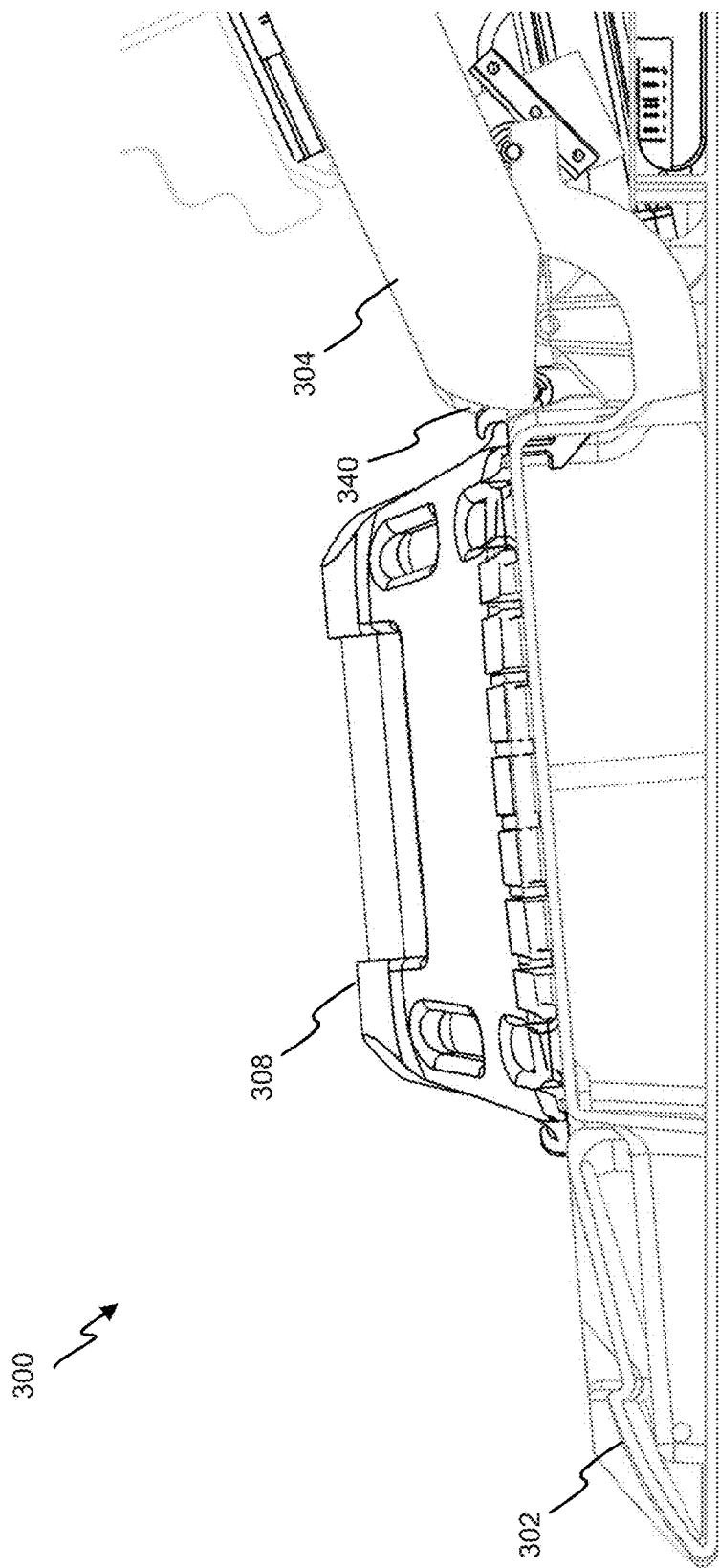
FIG. 3G depicts the elevation device of FIG. 3A in a lowered position.
Figure 3H:
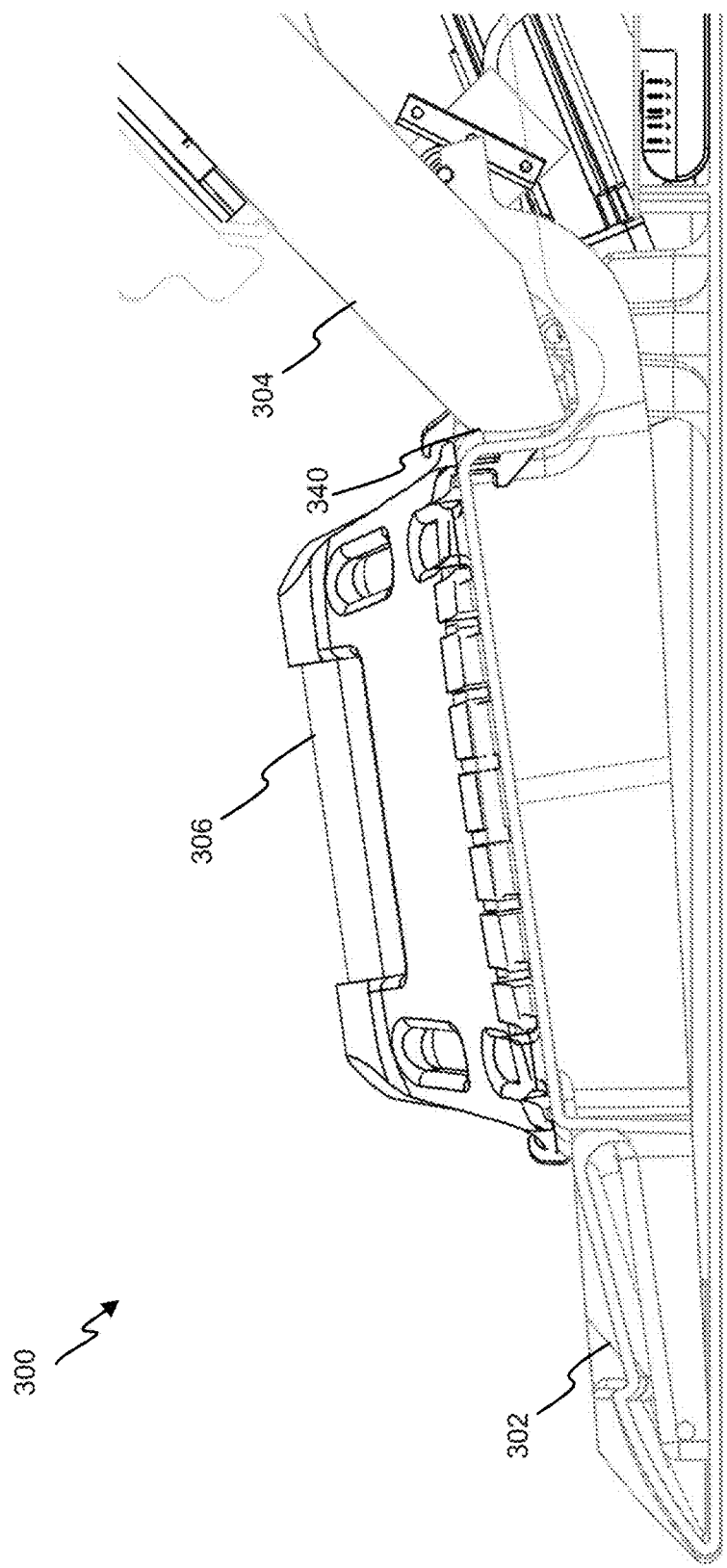
FIG. 3H depicts the elevation device of FIG. 3A in an elevated position.
Figure 31:
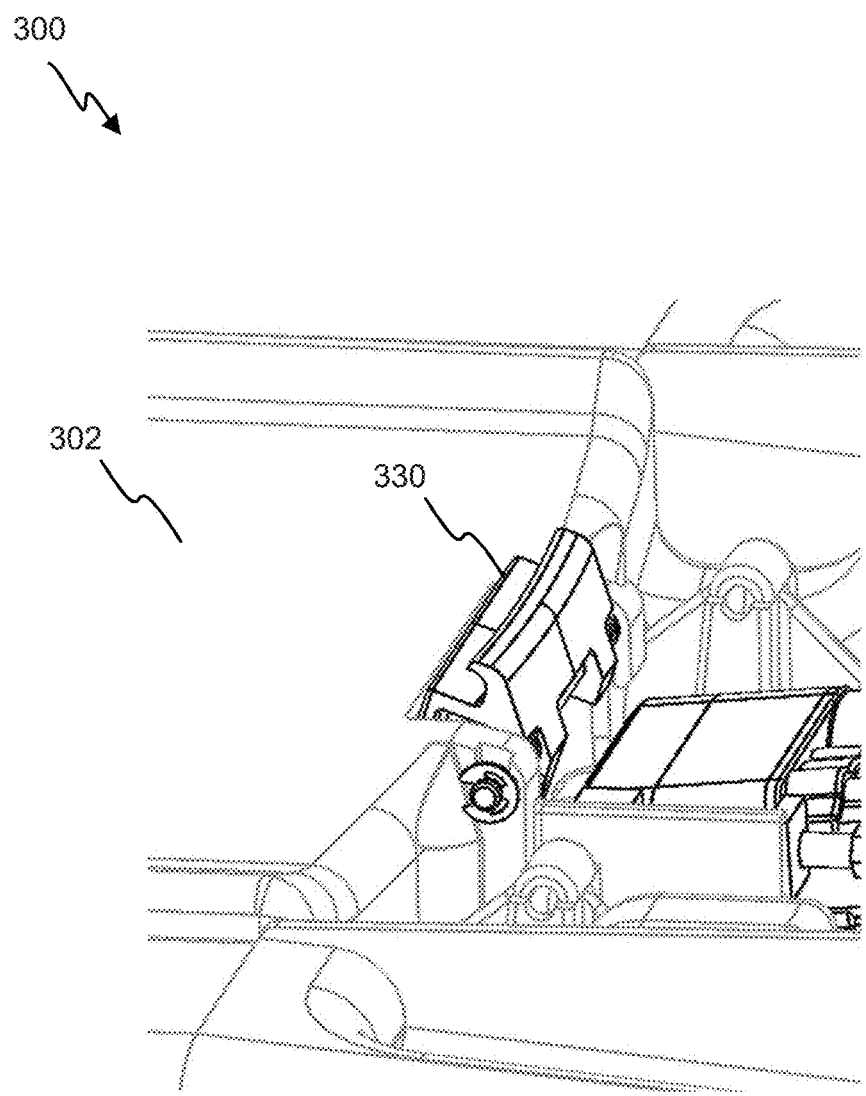

In some embodiments, the back plate 308 that is part of and/or is coupled with the upper support 304 in such a manner that an angle of the back plate 308 is adjustable relative to the base 302 and/or the upper support 304. The back plate 308 may be configured to adjust angularly to help combat thoracic shift to help maintain a chest compression device at a generally orthogonal to the sternum. The adjustment of the back plate 308 may create a separate elevation plane for the heart, with the head being elevated at a greater angle using the upper support 304 as shown in FIG. 3B. In some embodiments, the back plate 308 may be adjusted independently, while in other embodiments, adjustment of the back plate 308 is tied to the elevation of the upper support 304. For example, a back plate may include a roller (such as a v-groove bearing) positioned on an elevation track formed on or coupled with an underside of an upper support as illustrated in the embodiment discussed in relation to FIGS. 4G-4J of U.S. patent application Ser. No. 15/850,827, previously incorporated by reference. The roller may be positioned on a forward, raised portion of the elevation track. As the upper support 304 is elevated, the roller is forced upward by elevation track, thereby forcing an end of the back plate 308 proximate to the upper support 304 upwards. This causes the back plate 308 to tilt, thus maintaining the chest at a generally orthogonal angle relative to the chest compression device that is coupled with the back plate 308. Oftentimes, elevation track may be slanted from a raised portion proximate to the back plate 308 to a lowered portion. The elevation track may be tilted between about 4° and 20° to provide a measured amount of tilt relative to the thoracic shift expected based on a particular elevation level of the upper support 304. Typically, the back plate 308 will be tilted at a lower angle than the upper support 304 is inclined. Such simultaneous movement is also demonstrated in FIGS. 3G and 3H. In FIG. 3G, the upper support 304 is in the lowered position and the back plate 308 is in its original position. In FIG. 3H, the upper support 304 is elevated, which has caused the back plate 308 to have a corresponding forward tilt, which is less that than the degree of elevation of the upper support 304.

Figure 3J:
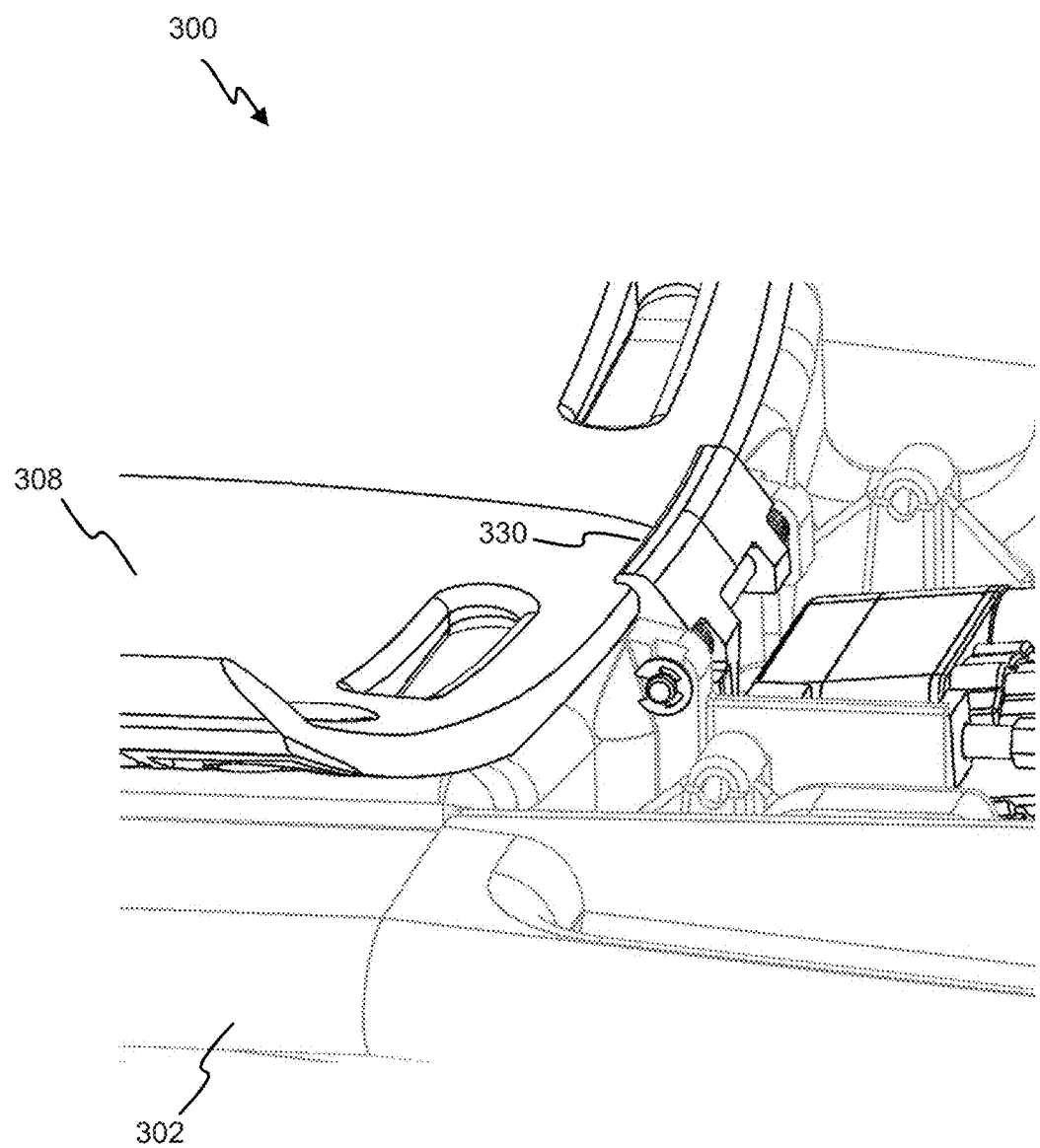
FIG. 3J depicts the latch of the elevation device of FIG. 3A.
Figure 3L:
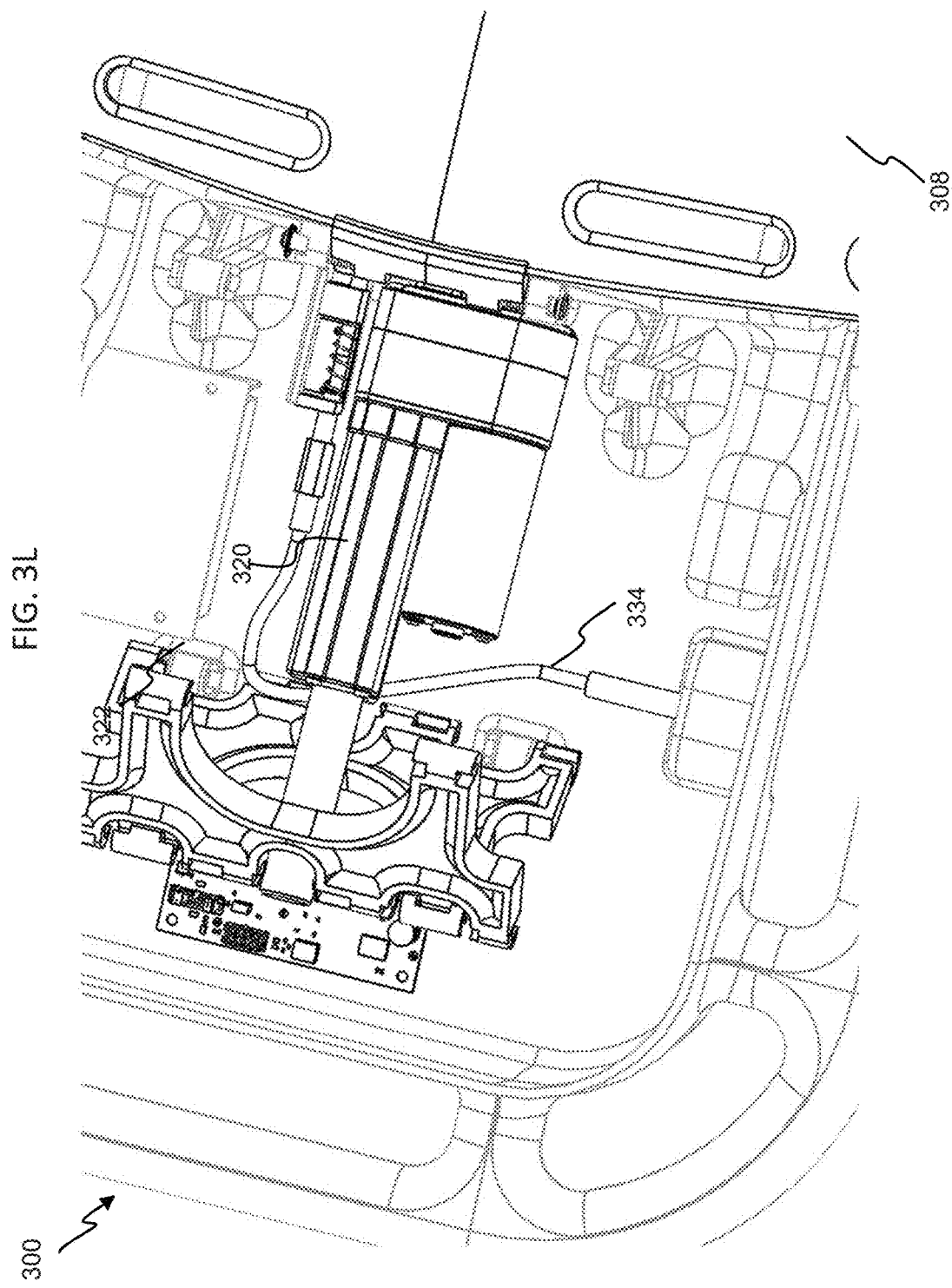
FIG. 3L depicts a release cable of the elevation device of FIG. 3A.

In some embodiments, the back plate may be removably coupled with the base 302 and/or the upper support 304. As shown in FIG. 3I, a latch 330 is provided beneath the back plate 308. The latch 330 may be spring biased such that a bottom surface of the latch 330 is able to receive a back edge of the back plate 308. The latch 330 may be pushed downward with the back plate 308 secured by a tip of the latch 330 until a spring-biased pin (not shown) slides along a bottom surface of the latch 330 and engages with a hole formed within a body of the latch 330. The pin secures the latch 330 in a locked position in which the back plate 308 is securely coupled with the base 302 and/or upper support as shown in FIG. 3J. A release knob 332 shown in FIG. 3K is coupled with the base 302 and may be used to draw the pin out of the hole formed in the body of latch 330 to release the back plate 308. For example, as shown in FIG. 3L, release knob 332 may be coupled to the pin via a flexible cable 334, similar to a brake cable on a bicycle. When knob 332 is pulled, the pin is drawn out of the hole and the spring force can push the latch 330 into a release position in which the back plate 308 may be removed from the base 302.

In some embodiments, the elevation device 300 may include a number of features that make the device more safe to operate. For example, as seen in FIG. 3A, elevation device 300 may include a vinyl (or other natural or synthetic material) cover 336 that may cover the moving components, such as the motor or actuator and/or slide mechanism. the cover 336 can extend and retract as the upper support 304 raises and lowers. For example, cover 336 may operate in a manner similar to a convertible top for an automobile, and may retract in a compact, accordion style manner when the upper support 304 is lowered. The upper support 304 of elevation device 304 may have a front surface 340 that is curved in a manner such that as the upper support 304 raises and lowers the front surface 340 stays approximately the same distance from the back plate 308. In other words, a gap between the two components remains generally constant, which eliminates any possible pinching hazard that could exist due to the relative movement between the two components.

In one embodiment, a controller and/or control system may adjust an actuation speed of a motor or other elevation mechanism to raise or lower the upper support 304 of the elevation device 300 within the necessary time frame. For example, medical personnel may set a desired elevation time, starting elevation angle, intermediate elevation angle(s), final elevation angle, rate of elevation, etc. The controller will then operate linear actuator 320, a motor, and/or other elevation mechanism to slowly raise the upper support 304 from a starting elevation angle to a final elevation angle over the selected time period. For example, the controller may be configured to elevate the head and thorax may be done in a sequence by 1) elevating the head and thorax over two or more sequential elevation steps and/or 2) elevating the head and thorax over a more prolonged period of time from the start of the elevation to the final height. In some embodiments, the controller may cause the chest compression device to perform CPR for a period of time (between about 30 seconds and 10 minutes, more commonly between about 2 minutes and 8 minutes, and more commonly between about 3 minutes and 6 minutes) while the individual is in a flat, supine position (or nearly supine, such as with the head and/or heart elevated slightly to an angle of less than about 5 degrees relative to horizontal) prior to causing the actuator to elevate the upper support 304 and the individual to an intermediate and/or final height. In some embodiments where the individual has been primed flat, the controller may perform an additional priming step at an intermediate elevation position prior to elevating the individual to the final/highest elevation position. In other embodiments, the individual may be primed by first elevating the individual's head and heart to one or more intermediate elevation positions (i.e. between about 10 and 25 degrees) and then performing chest compressions for a period of time prior to elevating the individual's heart and head to a final elevation position (i.e. between 20 and 45 degrees). The chest compressions may be continued during the elevation adjustment periods after each priming step.

The controller may also control the rate of elevation of the upper support 304. As just one example, the controller may maintain the elevation speed at a rate of not faster than 1° over each 0.3 second period. The lift speed may be linear and/or non-linear throughout each elevation step.

Blood drains rapidly from the head when the patient has no blood pressure and the head and upper body are elevated. As a result, there is a need to lower the head fairly rapidly to prevent blood loss in the brain if CPR is stopped while the head is elevated. Typically, this means that the patient's head and upper body may be elevated at a different rate than it is lowered. The patient's head may be lowered by the controller between about 1 and 10 seconds, and typically between about 1-5 seconds.

The controller may also be configured to cause the actuator to slowly and continuously raise the upper support 304 (and individual's heart, shoulders, and head) from a starting elevation position to a final elevation position. For example, a starting elevation position may include the individual being positioned in a generally flat, supine position (with the head elevated less than 5° relative to horizontal). The individual's head, shoulders, and heart may be slowly raised (linearly and/or non-linearly) from the starting elevation position to a position where the head is elevated between about 20 and 45 degrees relative to horizontal (an absolute elevation of the heart by about 5-10 cm and an absolute elevation of the head by about 15-25 cm, although these ranges may vary based on the age, size, and/or physiology of a specific individual) over a period of between about 30 seconds and 10 minutes, more commonly between 2 minutes and 8 minutes, and optimally between about 3 minutes and 6 minutes, while CPR is performed. For example, the head, shoulders, and heart may be raised at a rate of between about 2.25°/second and about 1.5°/minute. In other embodiments, an individual may be quickly raised to a starting elevation position of between about 8-15 degrees before slowly elevating the head, shoulders, and heart to a final elevation position over a period of between about 30 seconds and 10 minutes, more commonly between 2 minutes and 8 minutes, and optimally between about 3 minutes and 6 minutes, while CPR is performed.

In some embodiments, the controller may receive data from one or more physiological sensors and use this data to determine rates and timing of elevation and lowering. For example, the patient on the elevation device 300 may be monitored using an electrocardiogram (ECG). The ECG may detect a stable heart rhythm even if the individual has no palpable pulse. Based on this detection of the stable heart rhythm, it may be determined to stop the performance of chest compressions and to promptly lower the upper support 304. For example, once it is detected that the patient has a stable heart rhythm, the controller may alert medical personnel that chest compressions should be ceased, and may send a signal to the motor or other actuator to cause the upper support 304 to rapidly lower. In some embodiments, alerting medical personnel may involve producing a visual indicator, such as lighting up a light emitting diode (LED) or other light source and/or presenting a textual and/or image-based display on a screen of the elevation device 300. In one embodiment, upon detecting a stable heart rhythm, the controller may send a command to the automatic chest compression device that causes the chest compression device to stop the delivery of chest compressions and/or decompressions. In another embodiment, upon detecting the stable heart rhythm, the controller will alert medical personnel, who may then operate the elevation device 300 to lower the upper support 304. It will be appreciated that other sensors may be used in conjunction with the elevation device 300 to determine: when to start and/or stop CPR, when to elevate and/or lower a patient's upper body, a degree of elevation of the patient's upper body, a rate of elevation or lowering of the patient's upper body, and/or other parameters of CPR and/or ITPR.

The elevation device 300 elevates the head above the heart, with the level of elevation optionally varying depending upon the method of CPR. CPR itself is inherently inefficient, providing only about 20% of normal blood flow to the heart and brain. Elevation of the head is not safe during conventional CPR as it is not possible to consistently or safely push enough blood "uphill" to the head to take advantage of the effects of gravity of the venous side of the arterial-venous circuit that is integral to cerebral perfusion. Methods of CPR that generate the most forward flow provide the opportunity to elevate the head above the heart more than those methods that provide less forward flow. For example, active compression decompression (ACD) CPR with an impedance threshold device (ITD) can triple blood flow to the heart and brain compared with conventional manual CPR alone and therefore the head can be elevated higher and still get enough perfusion to take advantage of the effects of gravity with HUP CPR. By contrast, the head should not be elevated as much with conventional CPR and the ITD as forward blood flow without ACD CPR is less, and therefore too much elevation of the head could worsen outcomes. For these reasons the optimal head elevation may vary both depending upon the method of CPR used and the condition of the patient.

The relative vertical distance between the head and the heart is important as the amount of pressure needed to "lift" or pump the blood from the heart to the brain is related to this distance. Further, the vertical distance between the head and the heart affects the amount of cerebral perfusion. Although the amount of elevation of the head relative to the heart may vary depending upon the method of CPR (which is the mechanism used to pump the blood), it is generally preferred to have the head elevated relative to the heart by a distance in the range from about 2 cm to about 42 cm. In the specific case where ACD-CPR is being performed with an ITD, the distance may be in the range from about 5 cm to about 25 cm, for standard CPR with an ITD between about 5 cm and about 20 cm, for ACD CPR by itself between about 5 cm and about 20 cm, and with conventional or standard CPR between about 3 cm and about 15 cm. Further, the distance that the heart may be elevated relative to a support surface upon which the lower portion of the patient is resting (such as a table, floor, gurney, stretcher, or the ground) may be in the range from about 3 cm to about 20 cm (with ranges between about 4 cm and 10 cm being common), while the height of the head relative to the support surface may be in the range from about 5 cm to about 45 cm (with ranges between about 10 cm and 40 cm being common). When performing ACD-CPR+ITD, the distance that the heart may be elevated relative to a support surface upon which the patient is resting may be in the range from about 3 cm to about 20 cm, while the height of the head relative to the support surface may be in the range from about 5 cm to about 45 cm. Of course, these relative heights can also be thought of in terms of an angle of elevation of the upper body relative to the lower body when the patient is bent at the waist when performing CPR. Such angles are described herein. Typically, the angle between the patient's heart and brain is between 10 degrees and 40 degrees relative to horizontal to achieve the necessary elevation, although it will be appreciated that such angles are largely driven by the patient's physiology (height, distance between head and heart, etc.).

In some embodiments the heart will not be elevated. For example, a small head-only elevation device may be used that would only elevate the head, while allowing the heart to remain in the horizontal plane along with the lower body. Such elevation devices may be particular useful when performing CPR without the use of a CPR assist device/automated chest compression device as it reduces the amount of force needed to pump blood to the patient's brain during CPR. In such cases, the head would be raised to a distance in the range from about 5 to 20 cm relative to the heart (which is not elevated relative to the support surface).

In some embodiments, the controller be configured to detect a type of CPR being delivered and may automatically adjust an elevation of the heart and/or head based on the detected level of force. This may be done, for example, by allowing a user to input a type of CPR being performed into the elevation device 300. In other embodiments, such as those where a chest compression device is coupled with or formed integrally with the elevation device, the elevation device may communicate with the chest compression device to determine if the chest compression device is being used to deliver compressions and/or an amount of force being delivered and may make any necessary elevation adjustments based on this data. In other embodiments, one or more physiological sensors may be used to detect physiological parameters, such as cerebral perfusion pressure, intrathoracic pressure, and the like. This sensor data may be used to determine a compression force and/or otherwise determine how high to elevate the head and heart.

It should be noted that the elevation devices/head up devices (HUD) could serve as a platform for additional CPR devices and aids. For example, an automatic external defibrillator could be attached to the HUD or embodied within it and share the same power source. Electrodes could be provided and attached rapidly to the patient once the patient is place on the HUD. Similarly, ECG monitoring, end tidal $CO_2$ monitoring, brain sensors, a defibrillator, and the like could be co-located on the HUD. In addition, devices that facilitate the cooling of a patient could be co-located on the HUD to facilitate rapid cooling during and after CPR.

In addition or alternatively to one or more of the techniques described above, in some embodiments, the chest compression device will be coupled to a device to elevate the head and thorax that includes one or more support restraints (such as straps, belts, rods, cloth strips, and the like) to stabilize the patient on the elevation device.

It should be further noted that during the performance of CPR the compression rate and depth and force applied to the chest might vary depending upon whether the patient is in the flat horizontal plane or whether the head and thorax are elevated. For example, CPR may be performed with compressions at a rate of 80/min using active compression decompression CPR when flat but at 100 per minute with head and thorax elevation in order to maintain an adequate perfusion pressure to the brain when the head is elevated. Moreover, with head elevation there is better pulmonary circulation so the increase in circulation generated by the higher compression rates will have a beneficial effect on circulation and not "overload" the pulmonary circulation which could happen when the patient is in the flat horizontal plane.

It will be appreciated that some embodiments may utilize simplified elevation devices. For example, an elevation device may include only a base an upper support, and an actuator for raising and lowering the upper support relative to the base. The upper support may have one or more generally planar surfaces, with one or more of the surfaces optionally being contoured to match a shape of a patient's back. Additionally, the curved profile may make the support surface flexible. This flexibility helps when the elevation device 500 is used in conjunction with a chest compression device, as the flexibility ensures that the right amount force applied to the patient's chest. For example, a central portion of the upper support may flex in the presence of excessive force, thereby acting as a flexible back plate to absorb some of the force. For example, as a plunger of a chest compression device is pressed into the patient's chest, some force is transmitted through the patient to the upper support. The upper support may be configured to bend away from the patient if this transferred force exceeds a threshold. This allows for the delivery of compression at the appropriate depth for patients with differing chest wall sizes and stiffness's. This helps prevent broken ribs and/or other injuries to the patient caused by too much force being applied to the patient's chest, as the flexing back plate, rather than the ribs or other body structures, absorbs a significant portion of the excess force. Such a design is particularly useful when the elevation device is used in conjunction with a chest compression device such as the Lucas device, sold by Physio-Control, Inc. and/or the Zoll AutoPulse. However, it will be appreciated that the flexible upper support may be used in conjunction with any of the embodiments of elevation devices described herein. It should be appreciated that the portion of the elevation device under the heart and thorax could also contain force, pressure, impedance, and/or position sensors to provide feedback to the chest compression device, assuring the proper compression depth and force are delivered, even though the amounts needed to provide the proper CPR may differ from patient to patient and may change over time. In some embodiments, the chest compression device may be coupled with the elevation device 300 in such a manner that compressive and/or decompressive force from the chest compression device remains generally perpendicular (within 5 degrees) to the patient's sternum at all elevation positions.

In some embodiments, the patient's upper body may be elevated at a same angle on a single surface of the upper support, while in other embodiments the upper support may have two or more generally planar surfaces that elevate the heart and head at different angles relative to horizontal. The actuator may be manual and/or automatically driven with operating controls that enable the upper support to be to be raised and lowered in a controlled manner necessary to perform sequential elevation as described herein. For example, the elevation device may be fitted with controllers, motors, threaded rods, lead screws, pneumatic and/or hydraulic actuators, motor driven telescopic rods, other elevation mechanisms, and/or combinations thereof. In some embodiments, the motors may be coupled with a controller or other computing device. The controller may communicate with one or more input devices such as a keypad. This allows a user to select an angle and/or height of the heart and/or head to be raised using the motor and/or other actuator, along with a rate of elevation or other timing element of the elevation process. Additionally, the controller may be coupled with one or more sensors, such as flow and pressure sensors. Sensor inputs may be used to automatically control the motor and angle of the supports based on flow and pressure measurements. A type of CPR and/or ITP regulation may also be controlled using these and/or other sensor inputs. In some embodiments, the electro-mechanical lift mechanisms may include disengagement mechanisms that allow the elevation device to be operated manually. This allows the elevation device to be operable even if a power source for the electromechanical features is unavailable, such as when a battery is dead or when there is no power outlet or other power source available.

In some embodiments, the upper support may define an opening that is configured to receive a portion of a patient's head. This opening may help maintain the patient in the sniffing position for optimal airway management. Oftentimes, a head support may be included on the upper support. It will be appreciated that in some embodiments the head support may extend around the entire opening. The head support may be formed of contoured padding, such as foam padding, such that patients having heads of different sizes and shapes may be supported adequately by the single head support.

In some embodiments, the chest compression device and the elevation device may share a common power source. For example, the chest compression device or the elevation device may include a power source, such as a power cord and/or battery. The non-powered device may then plug into the other device to share the power source. In other embodiments, the chest compression device and the elevation device may be formed as a single device, with the elevation mechanism of the elevation device and the chest compression device both being wired to a single power source.

In some embodiments, the chest compression device and elevation device may be configured to communicate with each other. For example, one or more network or other data cables and/or wireless interfaces may couple processors and/or sensors of each device to one another. Data regarding elevation height, speed of elevation, speed of declination, CPR rate, force applied to the patient, and/or other data may be measured and shared between the devices. Additionally, data from physiological sensors may be shared with the elevation device and/or the chest compression device. This physiological data, such as ICP, blood flow data, blood pressure, intrathoracic pressure measurements, and the like may be used to control the various parameters such as elevation timing, elevation angle, chest compression depth and/or force, and the like.

Additionally, the chest compression device and/or elevation device may be configured to communicate with other devices, such as computers, mobile devices like mobile phones and tablet computers, e-readers, other medical equipment, such as electrocardiographs and defibrillators, and the like. To enable such communication, one or more wired and/or wireless communication networks may be established. For example, various data cables may be used to communicatively couple the chest compression device and/or elevation device to one or more remote devices. In some embodiments, the chest compression device and/or elevation device may include a wireless communications interface that is configured to communicate with one or more remote devices using WiFi, Bluetooth, 3G, 4G, LTE, and/or other wireless communications protocols.

In some embodiments, the elevation device may be coupled with a stretcher-like device for transport that has features that allow the heart and head to be elevated above the plane of the abdomen and lower extremities. For example, the stretcher or stretcher-like device may include rails or other rigid or semi-rigid support members that may be used to secure the elevation device and/or the chest compression device to the stretcher. The elevation device and/or the chest compression device may be coupled to the support members using clamps cables, and/or other securement mechanisms that may ensure the elevation device and/or the chest compression device do not shift relative to the stretcher.

In some embodiments, the elevation device may include a stowable shelf (not shown). The stowable shelf may be configured to be maintained in a stowed position in which most or all of the shelf is disposed within an interior of the elevation device, with only a handle and/or outer surface of the stowable shelf remaining exposed exteriorly of the elevation device. The stowable shelf may be extended outward into an extended position in which all or a large portion of the stowable shelf protrudes from a side of the wedge 300. This protruding portion may be used by medical personnel as a support for their knees so that the rescuer may be elevated relative to the ground and positioned properly for administering CPR. For example, the stowable shelf may be configured to elevate the rescuer to a height of between about 2 and 4 inches relative to the ground. Oftentimes, the stowable shelf may be positioned on a roller track or other sliding mechanism that enables the stowable shelf to be manipulated between the stowed position and the extended position.

Oftentimes it may be beneficial to gather data related to actual cases where CPR was performed. To gather this data, the elevation devices and/or intrathoracic pressure regulation devices may include sensors that are configured to measure and record various data related to the performance of CPR. Additional sensors and devices may also be used in conjunction with the elevation devices and/or intrathoracic pressure regulation devices to gather relevant data. Oftentimes this data may serve as feedback that drives various aspects of the CPR process. This data may also be useful in further advancing the science behind HUP CPR techniques, as well as to provide training data to help medical personnel learn and perfect the necessary techniques.

Figure 4:
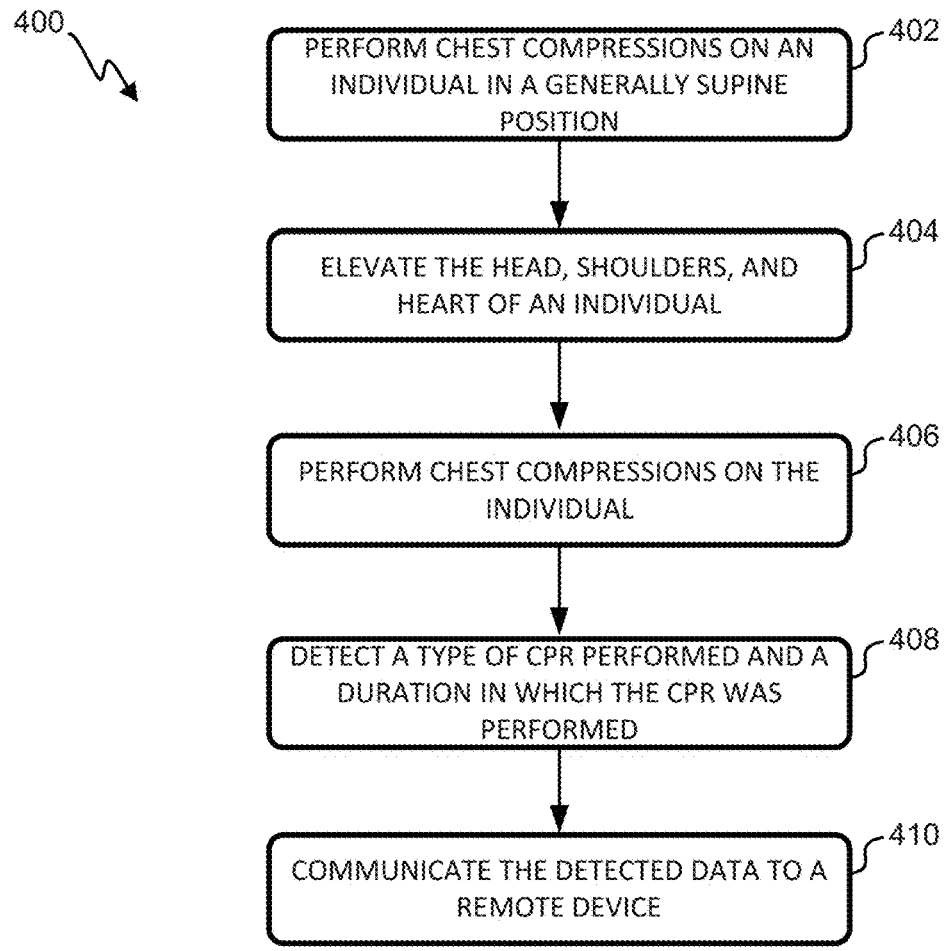
FIG. 4 is a flowchart of a process for performing CPR according to embodiments.

In some embodiments, an elevation device may be configured to communicate with a remote computer and/or a defibrillator. This allows details about the performance of CPR to be tracked and recorded, allowing for a review of the procedure. With such data, the EMS medical director could tell if the CPR was performed with HUP CPR, for what duration, and at what angle, among other data. As just one example, FIG. 4 depicts a process 400 for performing CPR and recording data related to the performance of CPR. Process 400 may be performed using any of the elevation devices described herein, such as elevation device 300. Process 400 may begin by performing chest compressions on an individual while the individual is in a generally supine position at block 402. The head, shoulders, and heart of an individual relative to a lower body of the individual using an elevation device at block 404. For example, the individual's upper body may be elevated from a starting position that is approximately supine (within about 5 degrees of horizontal) to a final elevation angle of between about 15° and 45° above horizontal. At block 406, chest compressions may be performed on the individual while the head, shoulders, and heart are elevated. One or more sensors of the elevation device may be used to detect a type of CPR performed and a duration that the type of CPR was performed at block 408. For example, force sensors on a support surface of the elevation device and/or at or near mounting positions of the chest compression device may be used to detect when chest compressions and/or decompressions are being delivered to the patient. This data may be used to derive a duration and type of CPR that was performed. Additional sensors may be used to detect the depth and force of chest compressions, elevation angles, timing of elevation of the upper body lowering of the upper body, timing of the performance of chest compressions, and the like. In some embodiments, the detected data may be communicated to a remote computing device at block 410, such as a laptop, personal computer, mobile phone, tablet computer and/or other computing device. The data may be communicated over a wired and/or wireless communications network. This allows the data to be received by the remote device and outputted on a display screen. The data can also be stored and then reviewed at a later time.

Figure 5:
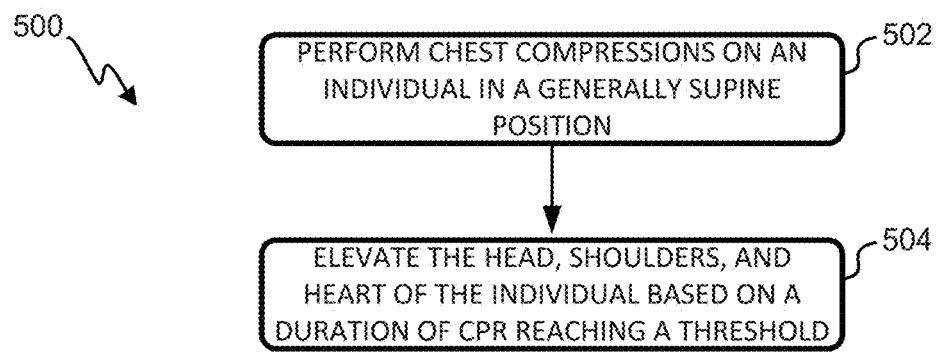
FIG. 5 is a flowchart of a process for performing CPR according to embodiments.

In another embodiment, feedback from one or more sensors may be used to assure CPR was performed at any given angle for a period of time. For example, a CPR protocol and/or an algorithm programmed onto the elevation device may take in sensor data and determine when to elevate and/or lower the individual's upper body. FIG. 5 is a flowchart depicting a process 500 for performing CPR based on such sensor feedback. Process 500 may be performed using the elevation devices described herein, such as elevation device 300. Process 500 may begin at block 502 by performing chest compressions on an individual in a generally supine position using a chest compression device. At block 504 the head, shoulders, and heart of an individual may be elevated relative to a lower body of the individual using an elevation device based on detecting that a duration of the performance of chest compressions on the individual in the generally supine position has reached a predetermined threshold. For example, after the sensors, such as force sensors coupled with a timer mechanism, detect that CPR was performed flat for a period of between about one and 3 minutes (typically about 2 minutes), the elevation device may be automatically triggered to elevate the patient's upper body. The performance of chest compressions is continued throughout elevation of the upper body. In some embodiments, a final angle of elevation of the head, shoulders, and heart is based on at least one physiological parameter detected by at least one sensor of the elevation device. For example, parameters such as blood flow directly assessed by end tidal CO2 may be measured using one or more sensors of the elevation device and/or on separate medical devices. In some embodiments, all sensor data, as well as information about the actual performance of supine and HUP CPR may be communicated to one or more remote devices over a wired and/or wireless data network.

Figure 6:
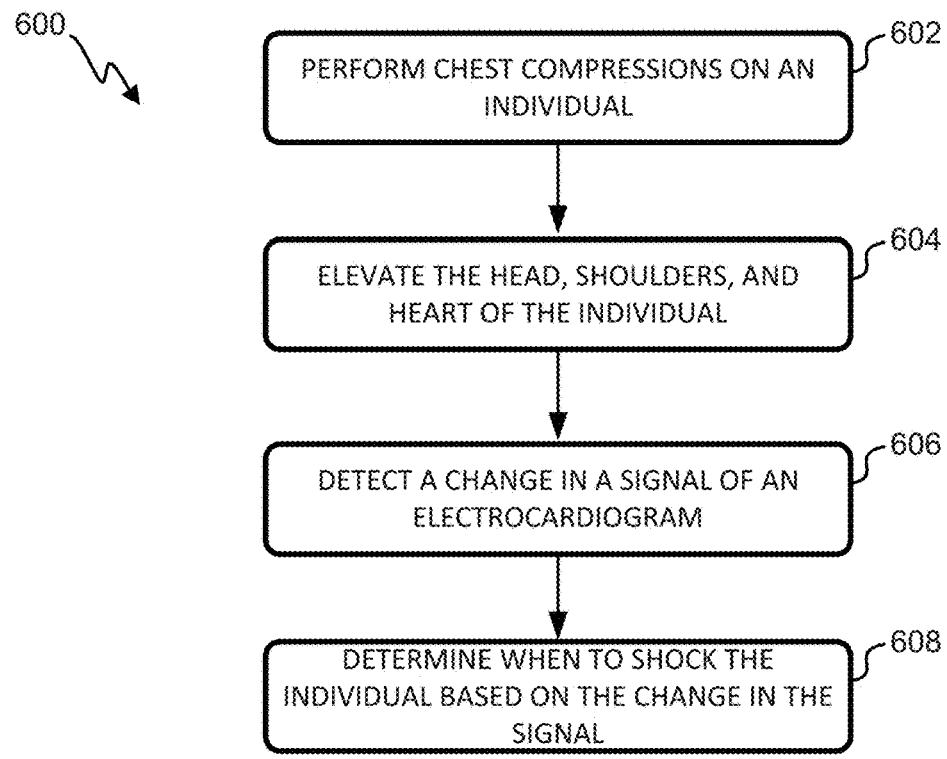
FIG. 6 is a flowchart of a process for performing CPR according to embodiments.

In some embodiments, information from an ECG may be used to determine when shocks need to be delivered using a defibrillator. FIG. 6 depicts a process 600 for performing CPR and delivering shocks based on ECG data. Process 600 may be performed using any of the elevation devices described herein, such as elevation device 300. Process 600 may begin at block 602 by performing chest compressions on an individual. The head, shoulders, and heart of the individual may be elevated relative to a lower body of the individual using an elevation device at block 604. At block 606, a change in a signal of an electrocardiogram (ECG) is detected while the head, shoulders, and heart are elevated. For example, a change in the ECG waveform or secondary ECG analysis based upon a change in the ECG signal (e.g. size, shape, frequency) after the start of head elevation may be detected. Based on this detected change, a time to shock the individual using a defibrillator may be determined at block 608. For example, the ventricular fibrillation waveform changes significantly with head up—the ventricular fibrillation waveform amplitude increases in size and then plateaus. When this amplitude increase and subsequent plateau is detected, the defibrillator may be triggered to shock the patient. Due to the improved coronary perfusion pressure and blood flow to the brain with HUP CPR, the ventricular muscle cells are more electrically active. With elevation of the head and thorax the distribution of blood flow through the lungs changes: more blood flow occurs as the lungs are less congested in the upper portions of the lungs compared to when the thorax is flat. As a result, the VF amplitude is greater and this can be detected and used to optimize the time of shock to provide the greatest likelihood of success.

In some embodiments, the defibrillator may be triggered automatically, while in other embodiments, the detection of the plateau may trigger an audio and/or visual notification that alerts medical personnel that the patient needs to be shocked.

Figure 7:
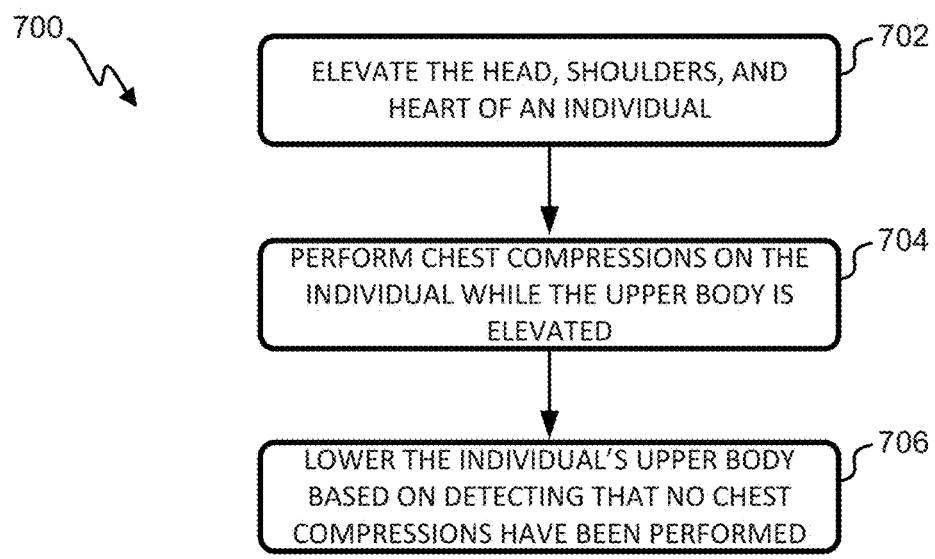
FIG. 7 is a flowchart of a process for performing CPR according to embodiments.

In some embodiments, a patient's upper body may be automatic lowered after the head up device senses no CPR for a predetermined threshold, such as about 5 seconds or more. This automatic lowering serves as a potential safety feature to ensure that the blood does not flow out of the brain if someone stops CPR with the patient's head elevated. FIG. 7 depicts a process 700 that utilizes such a safety mechanism. Process 700 may be performed using elevation devices described herein and may begin at block 702 by elevating the head, shoulders, and heart of an individual relative to a lower body of the individual using an elevation device. Chest compressions may be performed on the individual while the head, shoulders, and heart are elevated at block 704. At block 706, the head, shoulders, and heart may be lowered based on detecting, using a sensor of the elevation device, that no chest compressions have been performed for a predetermined threshold. For example, one or more force or other sensors may determine that no chest compressions have been delivered for at least about 5 seconds, and may trigger the elevation device to automatically lower the patient's head, shoulders, and heart to prevent blood from draining from the brain.

Figure 8:
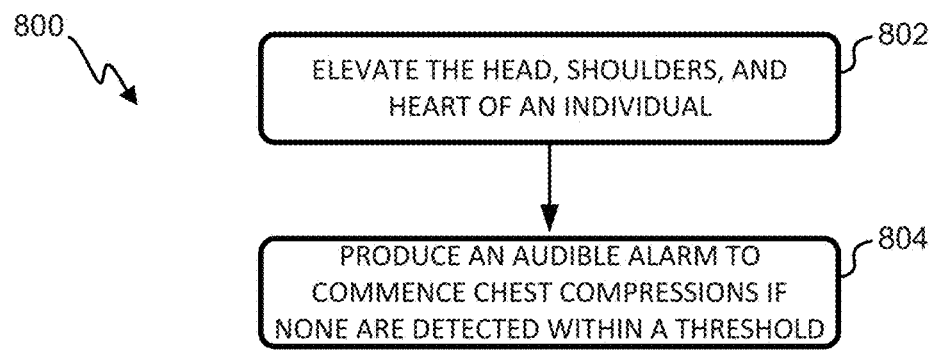
FIG. 8 is a flowchart of a process for performing CPR according to embodiments.

In some embodiments, verbal or other audio feedback may be provided to rescuers recommending they start and/or resume chest compressions once a pause is detected that is longer than a predetermined threshold. FIG. 8 depicts a process 800 that provides such audible feedback. Process 800 may begin at block 802 by elevating the head, shoulders, and heart of an individual relative to a lower body of the individual using an elevation device, such as elevation device 300. At block 804, an audible alarm may be produced by the elevation device that indicates that chest compressions should be commenced based on detecting, using a sensor of the elevation device, that no chest compressions have been performed for a predetermined threshold. Typically, this threshold is between about 5 and 10 seconds. In some embodiments, a compression sensor may be used to detect whether chest compressions have been delivered over a particular period of time. The audible alarm may include an alert sound and/or a recorded voice command instructing medical personnel to commence chest compressions. This alarm may be repeated until the compression sensor detects that chest compressions have been started.

Figure 9:
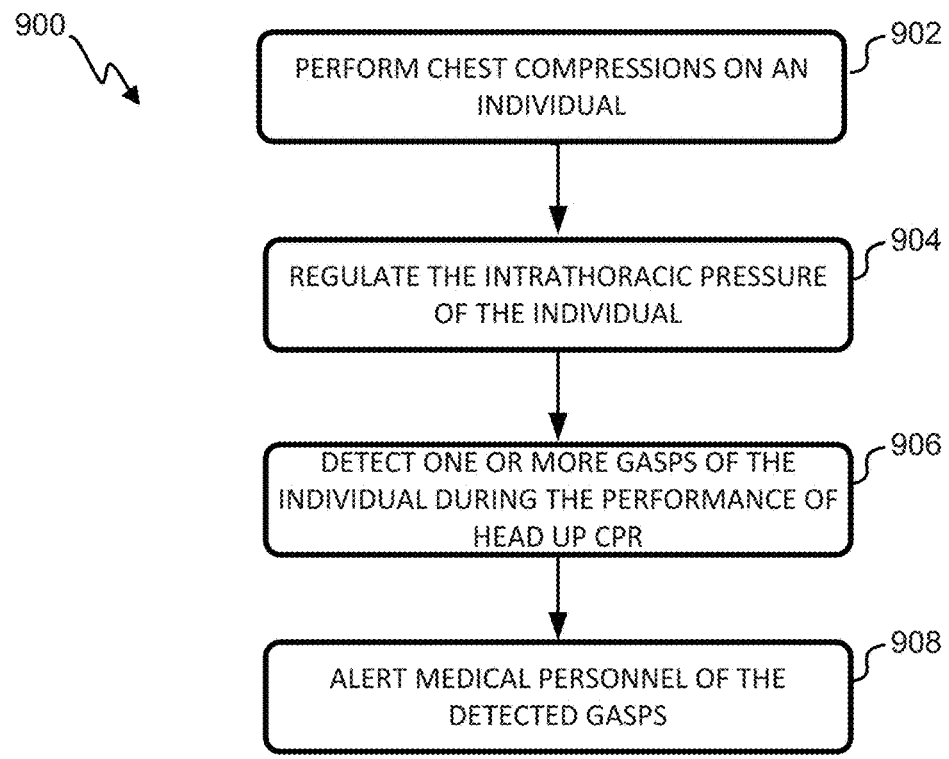
FIG. 9 is a flowchart of a process for performing CPR according to embodiments.

It has recently been recognized that the presence of gasping during CPR is a natural biomarker and is associated with a large increase in survival. The gasping reflex is similar to the effect achieved by an ITD during CPR: gasping lowers intrathoracic pressures, enhances venous return, lowers ICP, improves brain blood flow and enhances respiration. FIG. 9 depicts a process 900 for detecting the presence of gasping during CPR and alerting medical personnel of detected gasps. The medical personnel may then utilize this knowledge to adjust the administration of CPR and related procedures. Process 900 may begin at block 902 by performing chest compressions on the individual. The chest compressions may be performed with the patient being generally flat and/or while the head, shoulders, and heart are elevated, such as by using an elevation device similar to those described herein. At block 904, the intrathoracic pressure of the individual may be regulated during performance of CPR, such as by using an ITD. One or more gasps of the individual may be detected during performance of CPR at block 906. This may be done, for example, by using a device that detects gasping (number of gasps, the frequency of gasps, depth of the gasp, amount of airflow with the gasping, the amount of negative intrathoracic pressure generated with each gasp, and/or the timing of the gasps relative to the start of CPR and the start of head up, etc.) during performance of HUP CPR. In some embodiments, a gasping detector could be coupled with the ITD such that every time the patient gasps and creates a negative intrathoracic vacuum below the cracking pressure of the safety check valve of the ITD the safety check valve opens. A whistle may be placed on the safety check valve to alert the medical personnel of the gasp. An electronic pressure transducer may be placed in the ITD to enable recording of gasping. The medical personnel may be alerted of the detected gasps and/or other information such as a frequency of gasping and/or depth of respiration, at block 908. This data may also be recorded and made available for download and/or transmission to a remote device after the case.

It will be appreciated that various combinations of using sensor feedback to control aspects of HUP CPR and/or for data collection purposes may exist. For example, any combination of two or more of the processes described in relation to processes 400-900 are contemplated herein.

EXAMPLE 1

In a new study cerebral perfusion pressures (CerPP) and other physiological parameters were compared in pigs after 8 minutes of untreated ventricle fibrillation (VF). Aortic, right atrial, and intracranial pressures were measured during the compression and decompression phase of CPR. ACD+ ITD CPR was performed flat for 2 minutes and then each subject was randomized to 20, 30, or 40 degree head up tilt. This translates roughly to an absolute elevation of the heart by 3-5 cm, 4-8 cm, and 5-10 cm, respectively, and absolute elevation of the head by 5-12 cm, 12-18 cm, and 15-25 cm, respectively. Each pig received 6 minutes of CPR at each HUP angle, with the elevation angles being assigned in a random manner. It was discovered that elevating the head to a height of about 20 cm or 40 degrees head up is ultimately best, but it is best to start off elevating the head about 20 degrees for a period of time (in this case 6 minutes), then elevating to the next level (30 or 40 degrees). More specifically, the primary finding was that 40 degrees HUP was superior to 20 and 30, but only when 40 degrees HUP was randomized as the $2^{nd}$ or $3^{rd}$ intervention. It was not favorable when we randomized immediately to 40 degree HUP. Such findings are shown in FIGS. 10-13.

Figure 10:
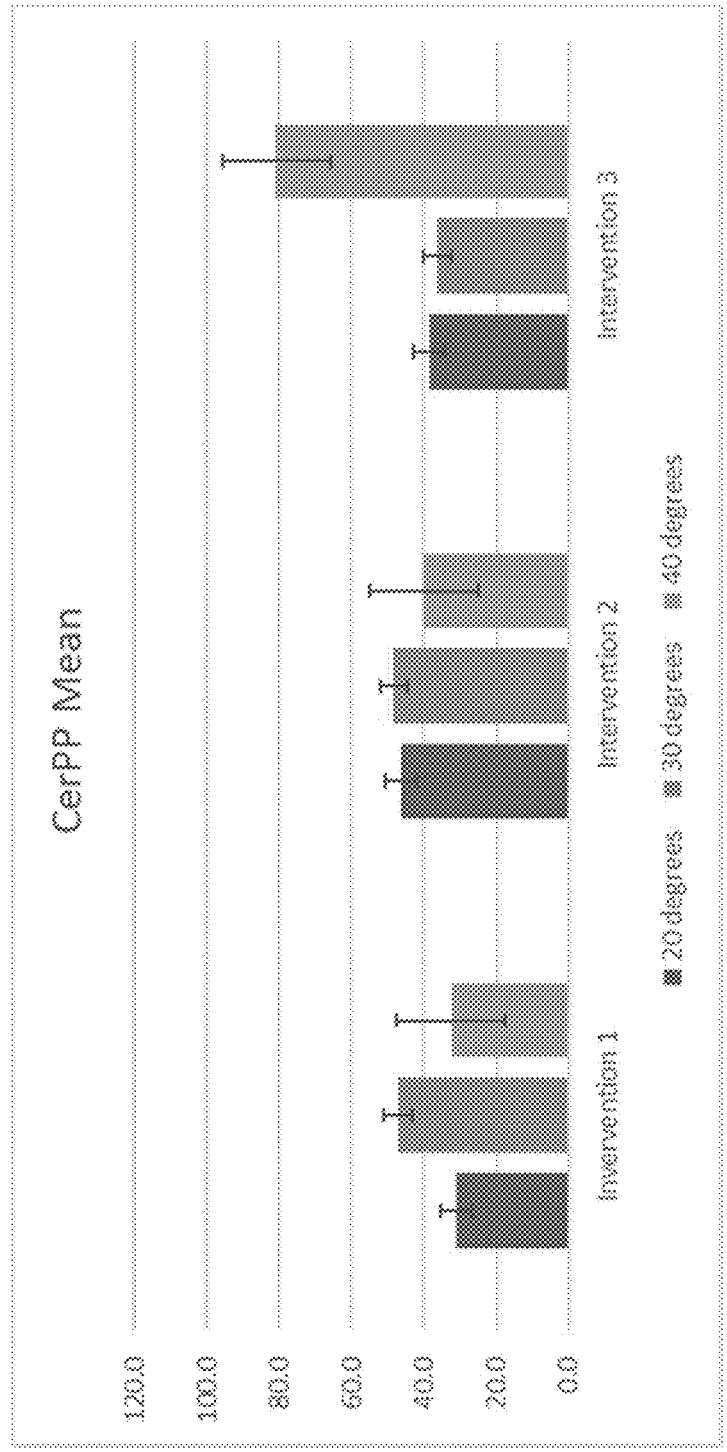
FIG. 10 is a graph depicting mean cerebral perfusion pressure associated with angle of elevation of the head and heart.
Figure 11:
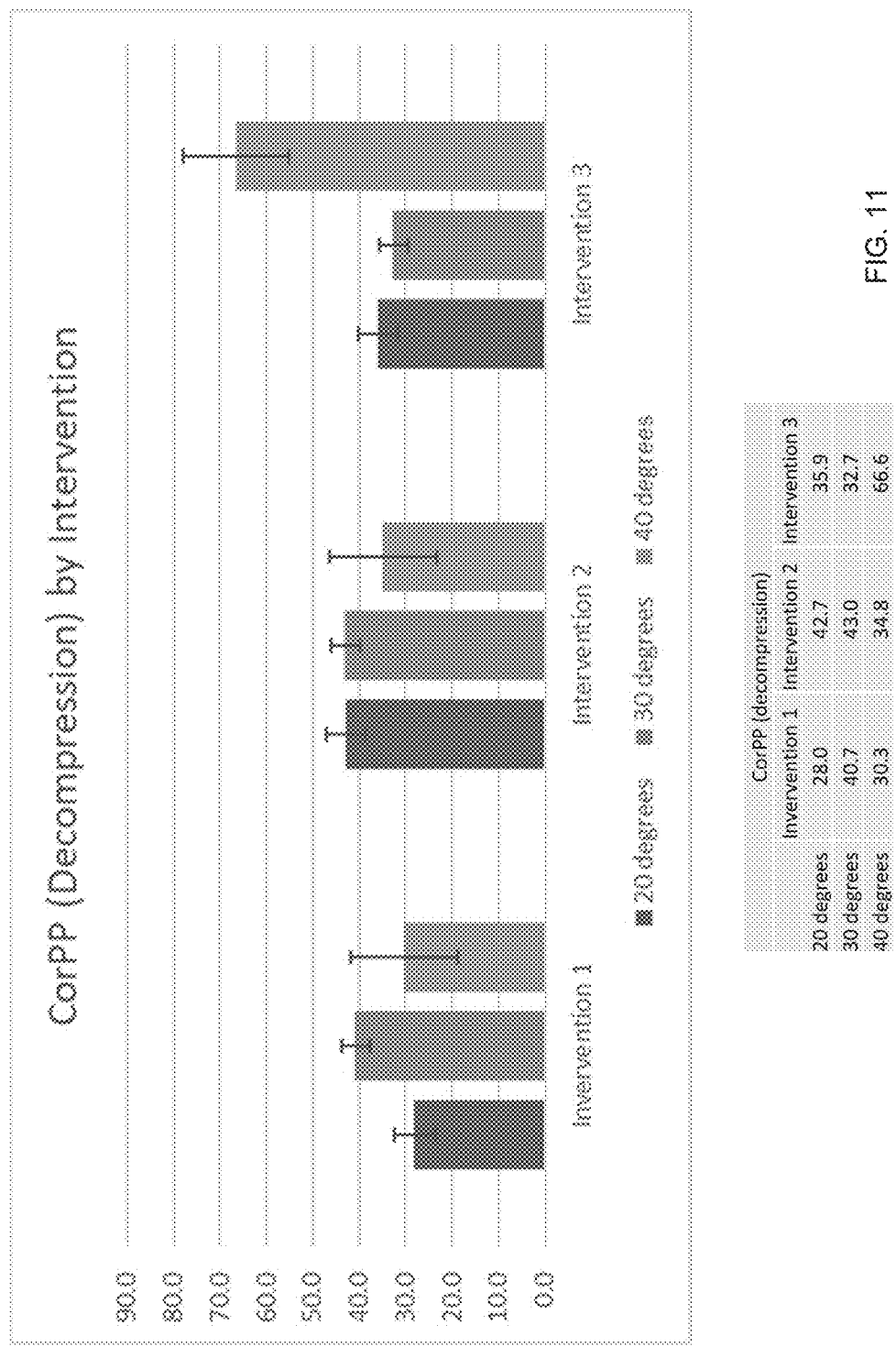
FIG. 11 is a graph depicting coronary perfusion pressure associated with an intervention order of various elevation positions of the head and heart.
Figure 12:
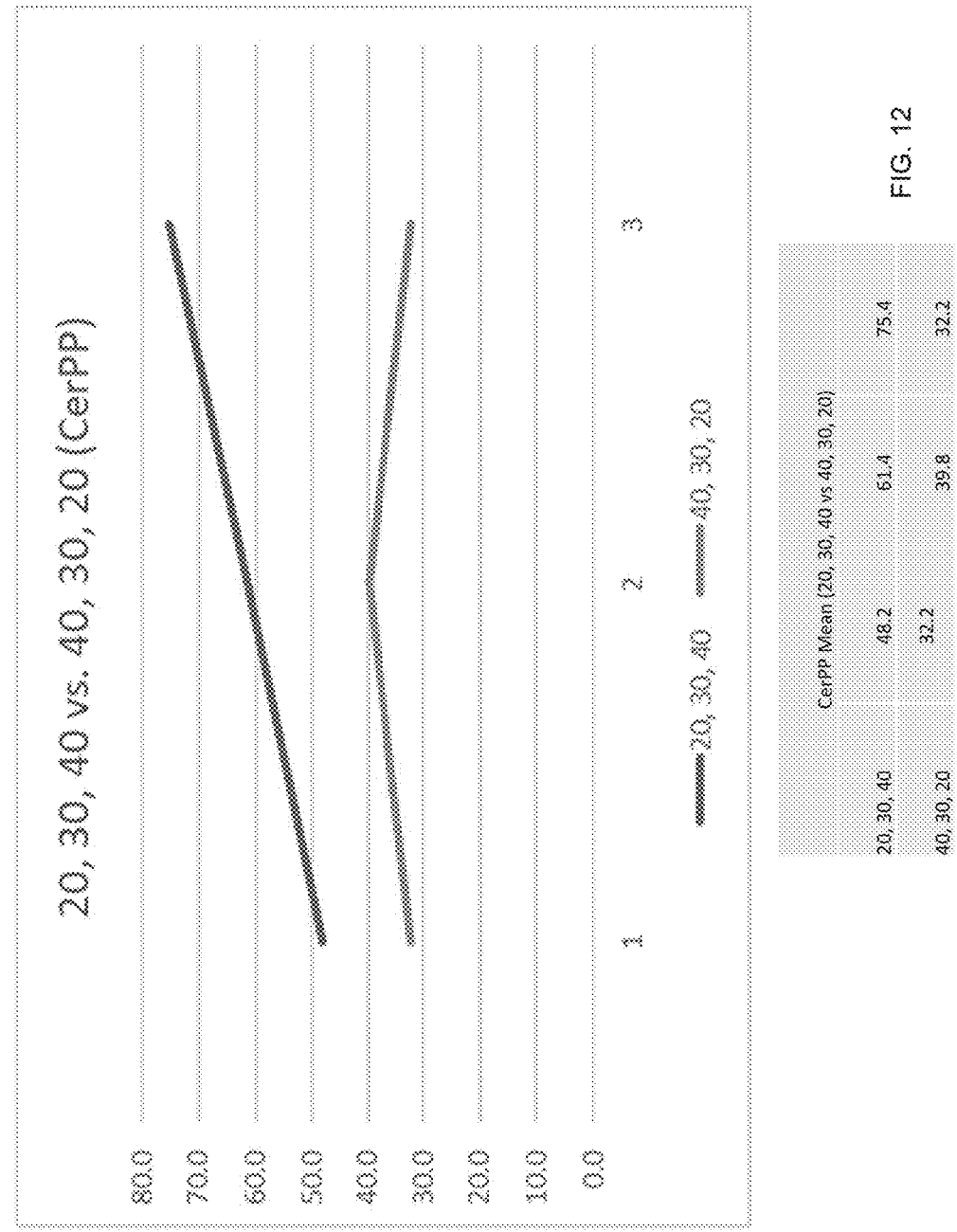
FIG. 12 is a graph depicting cerebral perfusion pressure associated with an order of the angle of elevation of the head and heart.
Figure 13:
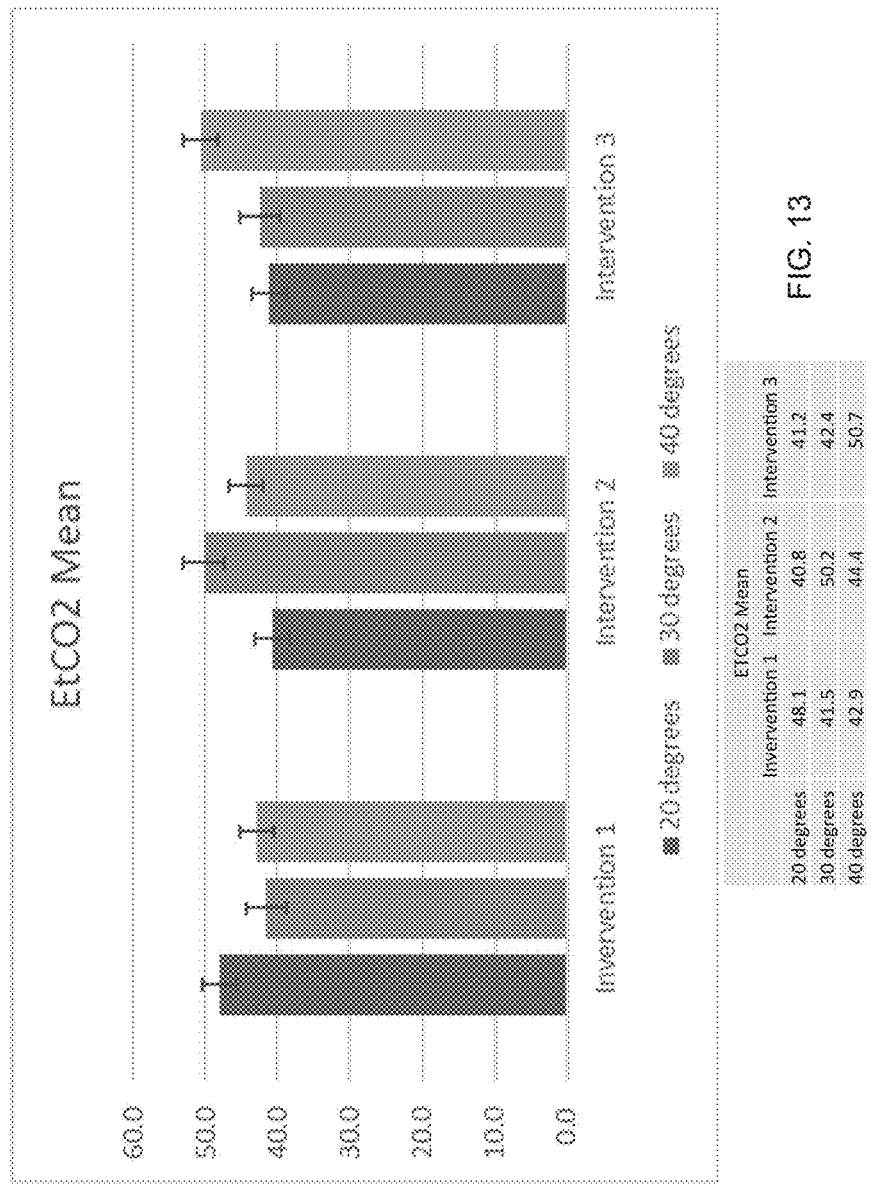
FIG. 13 is a graph depicting end tidal $CO_2$ mean values associated with elevation positions of the head and heart.

FIG. 10 depicts the mean CerPP by angle in each intervention. When 40 degrees was performed as the $3^{rd}$ intervention, the mean CerPP was over twice as high as when 20 or 30 degrees was used as the $3^{rd}$ intervention and nearly twice as high as any mean CerPP measured at any intervention. Similar results are shown in FIG. 11, which depicts the coronary perfusion pressure (CorPP) associated with each intervention. Again, 40 degrees of elevation on the $3^{rd}$ intervention provided significantly high results than any other trial. FIG. 12 shows the CerPP based on various intervention orders for each elevation angle. The highest CerPP levels were attained when the $3^{rd}$ intervention was at 40 degrees. Notably, going from 20, to 30, and then to 40 degrees head up provided the best cerebral perfusion and coronary perfusion pressures. FIG. 13 shows the end tidal $CO_2$ (ETCO$_2$) mean values for each of the head elevation levels in this study. ETCO$_2$ is considered an indirect marker of total body systemic blood circulation during CPR in animals and humans. In general, during CPR the more circulation there is, the more $CO_2$ generated metabolism is cleared from the blood stream. Consistent with the data presented in FIGS. 10-13, the highest ETCO$_2$ values were observed with a lower HUP CPR angle initially and the higher HUP CPR angles thereafter. In other words, blood circulation or blood flow was highest in the first intervention with 20° HUP CPR and highest after prolonged CPR with 40° HUP CPR. As illustrated by all the data, greater benefits are provided when the individual is primed prior to elevating the individual to the highest level.

Based on these results, it is clear that it is necessary to prime the body with a lower height or lesser angle, for several minutes for the system to be able to function optimally and to be able to get the full benefit of HUP CPR. By slowly raising the head and thorax during HUP CPR, in a sequential and graduated manner, rather than immediately elevating the individual to the highest/final angle, is best for this dynamic physiological system. There is due to the existence of some hysteresis in the system. In other words, it takes time for the whole circulatory system to adjust to head and heart elevation. Thus, it is critical to raise the head and heart in sequential steps and/or gradually to allowing the circulatory system an opportunity to adjust, thereby providing greater benefits and minimizes risks associated with HUP CPR.

EXAMPLE 2

Figure 14:
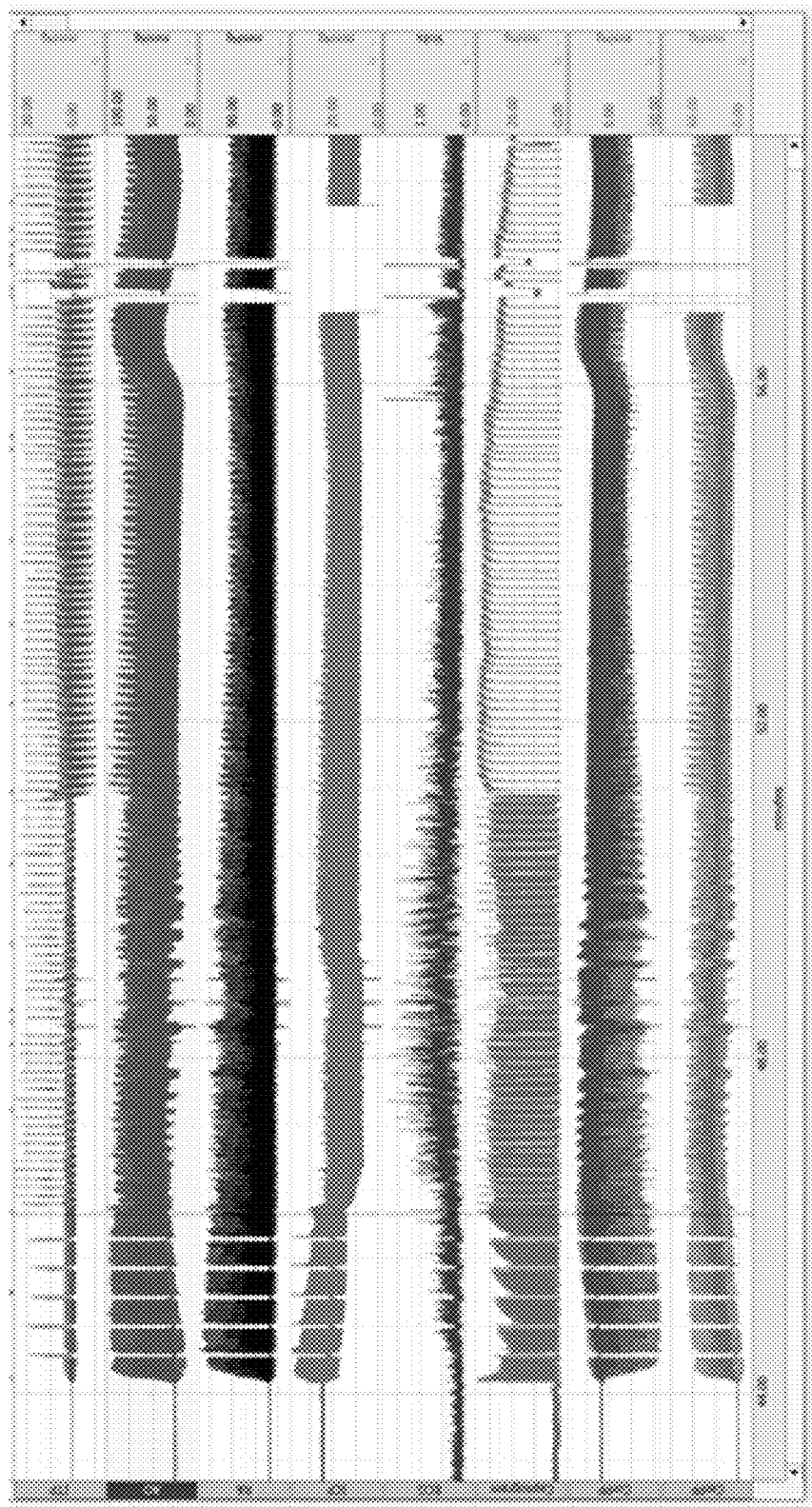
FIG. 14 shows an electrocardiograph taken from a study of HUP CPR in pigs.
Figure 15:
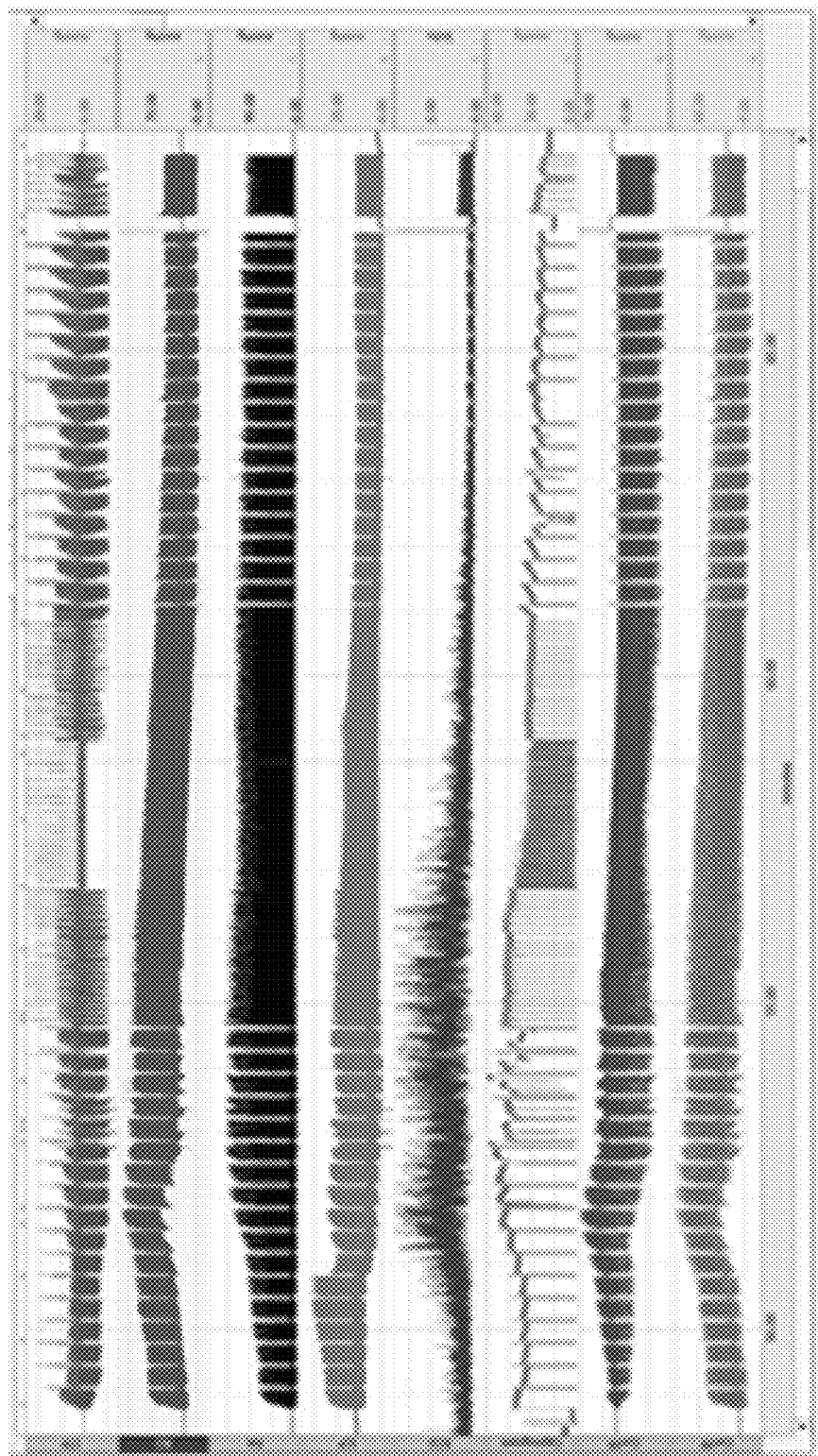
FIG. 15 shows an electrocardiograph taken from a study of HUP CPR in pigs.
Figure 16:
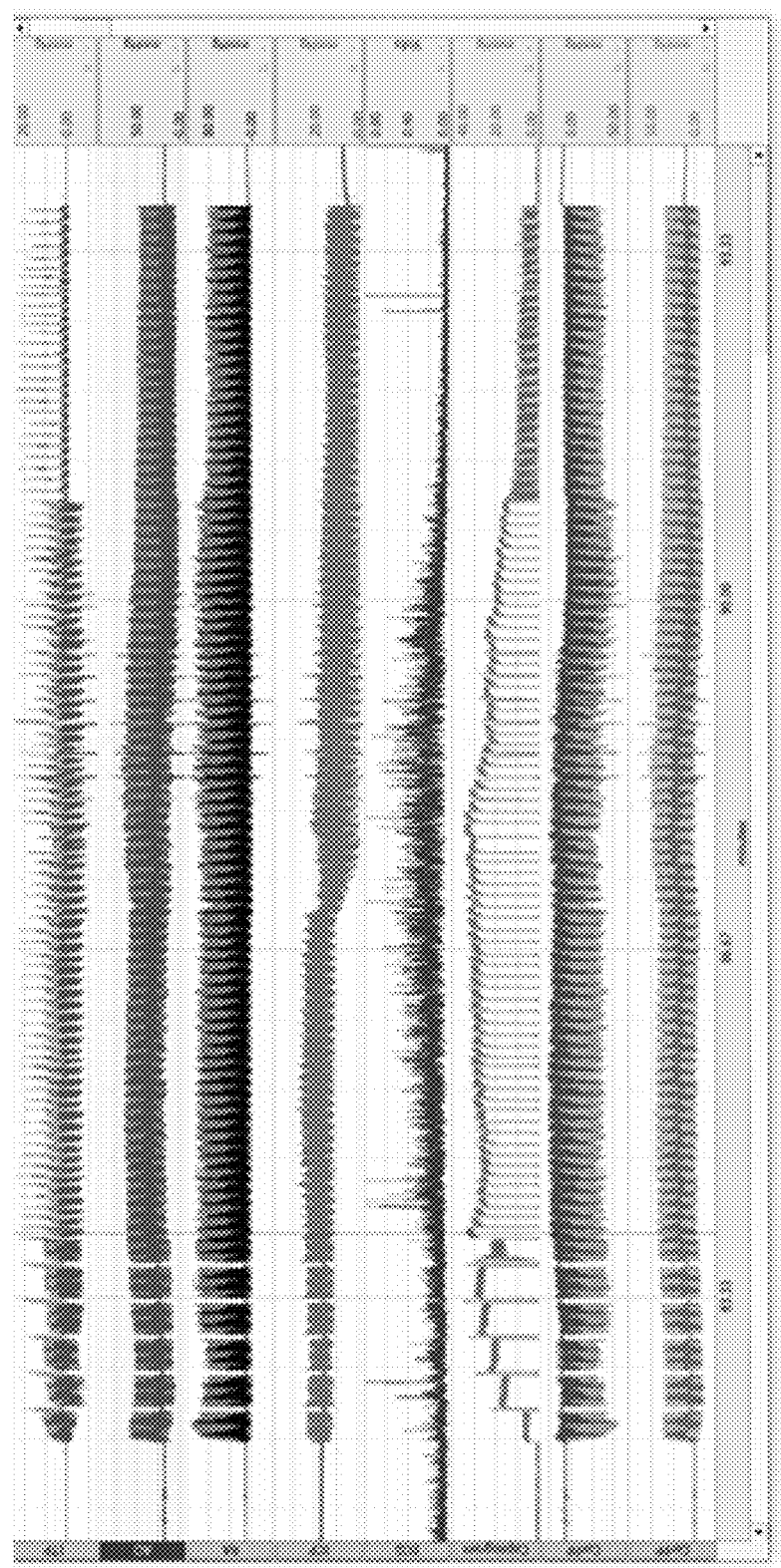
FIG. 16 shows an electrocardiograph taken from a study of HUP CPR in pigs.

Three studies were performed using pigs in which a number of parameters, such a ventricular fibrillation (VF) amplitude and frequency, were measured using an ECG. These studies involved performing ACD CPR+ITD in a supine position and an elevation position. As seen in the ECGs shown in FIGS. 14-16, the intracranial pressure drops quickly when the head is elevated. The ECG shows the change: there is an increase in the ECG amplitude during VF. The longer the wait before elevating the head, the less effect there was on VF amplitude (in study 3, HUP CPR was performed after 8 minutes of untreated VF and 2 minutes of CPR). Using such data, an optimal time to shock a person may be determined, using the commencement of HUP CPR as a starting point for the timer.

What is claimed is:

1. A method of increasing blood flow to the head, comprising:
   performing chest compressions to cause an individual's blood to circulate while the individual's heart and head are at a first elevation position;
   automatically adjusting the individual's heart and head to a second elevation position that is different than the first elevation position, wherein one or both of a timing of the adjusting and an elevation angle of the second elevation position are controlled based on data from one or more physiological sensors that are interfaced with the individual; and
   causing the individual's blood to circulate while the individual's heart and head are at the second elevation position.

2. The method of increasing blood flow to the head of claim 1, further comprising:
   causing the individual's blood to circulate during elevation of the individual's head and heart from the first elevation position to the second elevation position.

3. The method of increasing blood flow to the head of claim 1 performing chest compressions on the individual while regulating the individual's intrathoracic pressure to circulate the individual's blood.

4. The method of increasing blood flow to the head of claim 1, further comprising:
   actively regulating an intrathoracic pressure of the individual to create a negative intrathoracic pressure within the individual's chest while the individual's heart and heart are elevated at the second position.

5. The method of increasing blood flow to the head of claim 1, wherein:
   the one or more physiological sensors comprise one or more of a blood flow sensor, a blood pressure sensor, an end tidal CO2 sensor, or a cerebral oximetry sensor.

6. The method of increasing blood flow to the head of claim 1, wherein:
   adjusting the individual's heart and head to a second elevation position comprises raising or lowering the individual's heart and head.

7. The method of increasing blood flow to the head of claim 1, wherein:
   causing the individual's blood to circulate while the individual's heart and head are at the second elevation position is done at an increased rate relative to causing the individual's blood to circulate while the individual's heart and head are at the first elevation position.

8. A method of increasing blood flow to the head, comprising:
   priming an individual's circulatory system by performing chest compressions on the individual while the individual's heart, shoulders, and head are at a first elevation position;
   automatically elevating the individual's heart, shoulders, and head to a second elevation position while performing chest compressions, wherein one or both of a timing of the elevating and an elevation angle of the second elevation position are controlled based on data from one or more physiological sensors that are interfaced with the individual; and
   performing chest compressions on the individual while the individual's heart, shoulders, and head are at the second elevation position.

9. The method of increasing blood flow to the head of claim 8, wherein:
the first elevation position is between about 0 and 20 degrees above horizontal.

10. The method of increasing blood flow to the head of claim 8, wherein:
priming the individual's circulatory system is performed for a period of time between about 20 seconds and 10 minutes.

11. The method of increasing blood flow to the head of claim 8, further comprising:
with ongoing cardiopulmonary resuscitation elevating the individual's heart, shoulders, and head to a third height that is higher than the second height after performing chest compressions on the individual while the individual's heart, shoulders, and head are at the second height for an additional period of time.

12. The method of increasing blood flow to the head of claim 11, wherein:
the additional period of time is determined based on one or more measured physiological parameters.

13. The method of increasing blood flow to the head of claim 8, further comprising:
regulating an intrathoracic pressure of the individual while performing chest compressions.

14. The method of increasing blood flow to the head of claim 8, further comprising:
actively decompressing the individual's chest between each chest compression.

15. The method of increasing blood flow to the head of claim 8, wherein:
chest compressions are continuously performed while elevating the individual's heart, shoulders, and head to the second elevation position.

16. The method of increasing blood flow to the head of claim 8, wherein:
with ongoing cardiopulmonary resuscitation elevating the individual's heart, shoulders, and head to a second elevation position is performed at a rate of between about 2.25°/second and about 1.5°/minute.

17. The method of increasing blood flow to the head of claim 8, wherein:
the first elevation position comprises the individual being in a generally flat, supine position such that the individual's heart, shoulders, and head are generally aligned with a horizontal plane.

18. The method of increasing blood flow to the head of claim 8, wherein:
the first elevation position comprises a heart height of between about 3 cm and 8 cm above horizontal and a head height of between about 5 cm and 15 cm above horizontal; and
the second elevation position comprises a heart height of between about 5 cm and 15 cm above horizontal and a head height of between about 15 cm and 25 cm above horizontal.

19. The method of increasing blood flow to the head of claim 8, wherein:
the one or more physiological sensors comprise one or more of a blood flow sensor, a blood pressure sensor, an end tidal CO2 sensor, or a cerebral oximetry sensor.

20. A method of increasing blood flow to the head, comprising:
priming an individual's circulatory system by performing chest compressions on the individual while the individual's heart, shoulders, and head are at a first elevation position, wherein the individual is suffering cardiac arrest;
automatically elevating the individual's heart, shoulders, and head over a predetermined period of time to a second elevation position while performing chest compressions; and
performing chest compressions on the individual while the individual's heart, shoulders, and head are at the second elevation position.

21. The method of increasing blood flow to the head of claim 20, further comprising:
actively regulating an intrathoracic pressure of the individual to create a negative intrathoracic pressure within the individual's chest while the individual's heart and heart are elevated at the second position.

22. The method of increasing blood flow to the head of claim 20, wherein:
one or both of a timing of the elevating and an elevation angle of the second elevation position are controlled based on data from one or more physiological sensors that are interfaced with the individual.

23. The method of increasing blood flow to the head of claim 22, wherein:
the one or more physiological sensors comprise one or more of a blood flow sensor, a blood pressure sensor, an end tidal CO2 sensor, or a cerebral oximetry sensor.

24. The method of increasing blood flow to the head of claim 20, wherein the predetermined period of time is between about 20 seconds and 10 minutes.

25. The method of increasing blood flow to the head of claim 20, wherein the automatic elevation is performed using a motor.

26. A method of increasing blood flow to the head, comprising:
priming an individual's circulatory system by performing chest compressions on the individual while the individual's heart, shoulders, and head are at a first elevation position;
automatically elevating the individual's heart, shoulders, and head over a predetermined period of time to a predetermined second elevation position while performing chest compressions, wherein the predetermined period of time is between about 20 seconds and 10 minutes; and
performing chest compressions on the individual while the individual's heart, shoulders, and head are at the second elevation position.

* * * * *